United States Patent
Bailey et al.

(10) Patent No.: US 9,931,644 B2
(45) Date of Patent: Apr. 3, 2018

(54) SYSTEM AND METHOD FOR AUTOMATED SAMPLE PREPARATION

(71) Applicant: Becton, Dickinson and Company, Franklin Lakes, NJ (US)

(72) Inventors: Kevin Bailey, Cockeysville, MD (US); Christopher Embres, Bel Air, MD (US); Donald Gorelick, Nashua, NH (US); Timothy R. Hansen, Spring Grove, PA (US); Dwight Livingston, Fallston, MD (US); Andre Scherz, Baltimore, MD (US); Gerard Sevigny, Nashua, NH (US); Mark Talmer, Pepperell, MA (US); Tong Zhou, Ellicott City, MD (US); Spencer Lovette, Mount Vernon, NH (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 104 days.

(21) Appl. No.: 15/192,440

(22) Filed: Jun. 24, 2016

(65) Prior Publication Data

US 2016/0318040 A1 Nov. 3, 2016

Related U.S. Application Data

(62) Division of application No. 13/672,302, filed on Nov. 8, 2012, now Pat. No. 9,381,524.

(Continued)

(51) Int. Cl.
*B04B 5/04* (2006.01)
*G01N 35/02* (2006.01)
(Continued)

(52) U.S. Cl.
CPC ............ *B04B 5/0414* (2013.01); *B01D 43/00* (2013.01); *B04B 11/043* (2013.01);
(Continued)

(58) Field of Classification Search
CPC ............ G01N 2035/0425; G01N 2035/00495
See application file for complete search history.

(56) References Cited

U.S. PATENT DOCUMENTS 710,553 A 10/1902 Anderson
3,545,932 A 12/1970 Gilford
(Continued)

FOREIGN PATENT DOCUMENTS

DE 2343987 B1 1/1975
DE 2637273 A1 2/1978
(Continued)

OTHER PUBLICATIONS

U.S. Appl. No. 61/557,011, filed Nov. 8, 2011.

*Primary Examiner* — P. Kathryn Wright
(74) *Attorney, Agent, or Firm* — Botos Churchill IP Law LLP

(57) ABSTRACT

A system for automatically processing a biological specimen is provided that includes an elevator comprising a plurality of shelves configured to receive a plurality of sample trays. The trays may comprise a plurality of sample containers containing a sample and having a plurality of respective caps engaged therewith. The trays may further include a plurality of centrifuge tube racks each containing a plurality of centrifuge tubes. The system may include a first transport mechanism, a second transport mechanism and a third transport mechanism. The system may include a chain-of-custody device configured to read identifiers on each of the containers. The system may also include a pipetting device (Continued)

configured to remove a portion from the sample containers and dispense the sample into the centrifuge tubes.

19 Claims, 30 Drawing Sheets

Related U.S. Application Data

(60) Provisional application No. 61/556,994, filed on Nov. 8, 2011.

(51) Int. Cl.
- B01D 43/00 (2006.01)
- B04B 11/04 (2006.01)
- G01N 35/04 (2006.01)
- G01N 35/00 (2006.01)

(52) U.S. Cl.
CPC .......... *G01N 35/026* (2013.01); *G01N 35/04* (2013.01); *G01N 2035/00495* (2013.01); *G01N 2035/0405* (2013.01); *G01N 2035/0425* (2013.01); *G01N 2035/0465* (2013.01)

(56) References Cited

U.S. PATENT DOCUMENTS

| | | | |
|---|---|---|---|
| 3,754,444 A | 8/1973 | Ure et al. |
| 4,439,319 A | 3/1984 | Rock |
| 4,705,630 A | 11/1987 | Gordon et al. |
| 4,772,558 A | 9/1988 | Hammann |
| 4,824,641 A | 4/1989 | Williams |
| 4,835,707 A | 5/1989 | Amano et al. |
| 4,859,610 A | 8/1989 | Maggio |
| 4,927,545 A | 5/1990 | Roginski |
| 5,286,959 A | 2/1994 | Demachi |
| 5,297,599 A | 3/1994 | Bucheli |
| 5,363,885 A | 11/1994 | McConnell et al. |
| 5,370,128 A | 12/1994 | Wainwright |
| 5,403,551 A | 4/1995 | Galloway et al. |
| 5,417,922 A | 5/1995 | Markin et al. |
| 5,427,743 A | 6/1995 | Markin |
| 5,431,884 A | 7/1995 | McDonough et al. |
| 5,455,006 A | 10/1995 | Aota et al. |
| 5,472,669 A | 12/1995 | Miki et al. |
| 5,483,843 A | 1/1996 | Miller et al. |
| 5,525,298 A | 6/1996 | Anami |
| 5,578,494 A | 11/1996 | Clark et al. |
| 5,623,415 A | 4/1997 | O'Bryan et al. |
| 5,637,854 A | 6/1997 | Thomas |
| 5,665,309 A | 9/1997 | Champseix et al. |
| 5,672,317 A | 9/1997 | Buhler et al. |
| 5,735,387 A | 4/1998 | Polaniec et al. |
| 5,814,276 A | 9/1998 | Riggs |
| 5,846,489 A | 12/1998 | Bienhaus et al. |
| 5,888,831 A | 3/1999 | Gautsch |
| 5,945,070 A | 8/1999 | Kath et al. |
| 5,948,360 A | 9/1999 | Rao et al. |
| 5,966,309 A | 10/1999 | O'Bryan et al. |
| 5,968,731 A | 10/1999 | Layne et al. |
| 6,056,921 A | 5/2000 | Rao et al. |
| 6,060,022 A | 5/2000 | Pang et al. |
| 6,081,326 A | 6/2000 | Rousseau et al. |
| 6,096,562 A | 8/2000 | Bunn et al. |
| 6,216,340 B1 | 4/2001 | Fassbind et al. |
| 6,257,091 B1 | 7/2001 | Cohen et al. |
| 6,267,927 B1 | 7/2001 | Pomar Longedo et al. |
| 6,277,646 B1 | 8/2001 | Guirguis et al. |
| 6,290,907 B1 | 9/2001 | Takahashi et al. |
| 6,291,234 B1 | 9/2001 | Raz et al. |
| 6,293,750 B1 | 9/2001 | Cohen et al. |
| 6,327,377 B1 | 12/2001 | Rutenberg et al. |
| 6,360,792 B1 | 3/2002 | Ganz et al. |
| 6,374,982 B1 | 4/2002 | Cohen et al. |
| 6,383,820 B1 | 5/2002 | Bunn et al. |
| 6,398,031 B1 | 6/2002 | Frezza |
| 6,398,281 B1 | 6/2002 | Heimberg |
| 6,455,002 B1 | 9/2002 | Jokes et al. |
| 6,458,324 B1 | 10/2002 | Schinzel |
| 6,562,299 B1 | 5/2003 | Ostgaard et al. |
| 6,572,824 B1 | 6/2003 | Ostgaard et al. |
| 6,589,749 B1 | 7/2003 | Guirguis |
| 6,637,473 B2 | 10/2003 | Ganz et al. |
| 6,651,305 B2 | 11/2003 | Fassbind et al. |
| 6,680,027 B2 | 1/2004 | Kang et al. |
| 6,803,239 B2 | 10/2004 | Bunn et al. |
| 6,843,962 B2 | 1/2005 | Haslam et al. |
| 6,883,958 B2 | 4/2005 | Mayer |
| 6,887,428 B2 | 5/2005 | Wernz et al. |
| 6,974,294 B2 | 12/2005 | Pressman et al. |
| 6,998,094 B2 | 2/2006 | Haslam et al. |
| 7,097,057 B2 | 8/2006 | Classens |
| 7,112,303 B2 | 9/2006 | Itoh |
| 7,141,213 B1 | 11/2006 | Pang et al. |
| 7,163,115 B2 | 1/2007 | Whitley |
| 7,282,182 B2 | 10/2007 | Dale et al. |
| 7,284,900 B2 | 10/2007 | Mayer |
| 7,303,725 B2 | 12/2007 | Reinhardt et al. |
| 7,316,805 B1 | 1/2008 | Viola et al. |
| 7,352,889 B2 | 4/2008 | Ganz et al. |
| 7,377,027 B2 | 5/2008 | Mayer |
| 7,392,949 B2 | 7/2008 | Itoh |
| 7,413,551 B2 | 8/2008 | Decker et al. |
| 7,435,599 B2 | 10/2008 | Ostgaard et al. |
| 7,470,404 B2 | 12/2008 | Kang et al. |
| 7,556,777 B2 | 7/2009 | Victor |
| 7,569,189 B2 | 8/2009 | Jacobs et al. |
| 7,572,638 B2 | 8/2009 | Pressman et al. |
| 7,579,190 B2 | 8/2009 | Ostgaard et al. |
| 7,587,952 B2 | 9/2009 | Dale et al. |
| 7,604,999 B2 | 10/2009 | Bierre et al. |
| 7,635,246 B2 | 12/2009 | Neeper et al. |
| 7,648,680 B2 | 1/2010 | Anderson et al. |
| 7,666,357 B2 | 2/2010 | Sattler et al. |
| 7,666,359 B2 | 2/2010 | Sattler et al. |
| 7,670,553 B2 | 3/2010 | Babson |
| 7,670,554 B2 | 3/2010 | Chow et al. |
| 7,674,434 B2 | 3/2010 | Sakal et al. |
| 7,731,903 B2 | 6/2010 | Sattler et al. |
| 7,771,662 B2 | 8/2010 | Pressman et al. |
| 7,793,842 B2 | 9/2010 | Neeper et al. |
| 7,795,036 B2 | 9/2010 | Johnson et al. |
| 7,799,560 B2 | 9/2010 | Wilson et al. |
| 7,807,476 B2 | 10/2010 | Pressman et al. |
| 7,823,745 B2 | 11/2010 | Esser et al. |
| 7,824,921 B1 | 11/2010 | Levy |
| 7,824,922 B2 | 11/2010 | Kacian et al. |
| 7,846,395 B2 | 12/2010 | Shaw |
| 7,871,568 B2 | 1/2011 | Liang et al. |
| 7,887,758 B2 | 2/2011 | Ostgaard et al. |
| 7,910,067 B2 | 3/2011 | Knight et al. |
| 7,963,900 B2 | 6/2011 | Miller |
| 2002/0107499 A1 | 8/2002 | Funk |
| 2003/0026732 A1 | 2/2003 | Gordon et al. |
| 2003/0044991 A1 | 3/2003 | Haslam et al. |
| 2003/0059347 A1 | 3/2003 | Ostgaard et al. |
| 2003/0087443 A1 | 5/2003 | Pressman et al. |
| 2003/0089731 A1 | 5/2003 | Mayer et al. |
| 2003/0091473 A1 | 5/2003 | Downs et al. |
| 2003/0099580 A1 | 5/2003 | Pressman et al. |
| 2003/0100125 A1 | 5/2003 | Pressman et al. |
| 2003/0109804 A1 | 6/2003 | Auerbach et al. |
| 2004/0047765 A1 | 3/2004 | Gordon et al. |
| 2004/0091401 A1 | 5/2004 | Golabek et al. |
| 2004/0180427 A1 | 9/2004 | Chang |
| 2005/0070873 A1 | 3/2005 | Johnson |
| 2006/0120834 A1 | 6/2006 | Pressman et al. |
| 2006/0120835 A1 | 6/2006 | Pressman et al. |
| 2007/0005169 A1 | 1/2007 | Rohnert et al. |
| 2007/0059209 A1 | 3/2007 | Pang et al. |
| 2007/0134130 A1 | 6/2007 | Hutchins et al. |
| 2007/0151212 A1 | 7/2007 | Mayer et al. |
| 2007/0287193 A1 | 12/2007 | Pressman et al. |
| 2008/0209709 A1 | 9/2008 | Mayer |

(56) References Cited

U.S. PATENT DOCUMENTS

| | | |
|---|---|---|
| 2008/0286831 A1 | 11/2008 | Liang |
| 2008/0307904 A1 | 12/2008 | Pressman et al. |
| 2009/0003981 A1* | 1/2009 | Miller ................... B65G 1/04 414/267 |
| 2009/0047179 A1 | 2/2009 | Ping et al. |
| 2009/0142844 A1 | 6/2009 | Le Comte |
| 2009/0168160 A1 | 7/2009 | Guiney et al. |
| 2009/0233331 A1 | 9/2009 | Ostgaard et al. |
| 2009/0275076 A1 | 11/2009 | Knesel et al. |
| 2009/0324370 A1 | 12/2009 | Eberle |
| 2010/0004779 A1 | 1/2010 | Markin |
| 2010/0018330 A1 | 1/2010 | Marty et al. |
| 2010/0028124 A1 | 2/2010 | Lackner et al. |
| 2010/0028203 A1 | 2/2010 | Frey et al. |
| 2010/0049358 A1 | 2/2010 | Koch et al. |
| 2010/0083772 A1 | 4/2010 | Tanaka |
| 2010/0089925 A1 | 4/2010 | Peltier |
| 2010/0124780 A1 | 5/2010 | Larkin |
| 2010/0126286 A1 | 5/2010 | Self et al. |
| 2010/0128944 A1 | 5/2010 | Zahniser et al. |
| 2010/0132484 A1 | 6/2010 | Schacher et al. |
| 2010/0170336 A1 | 7/2010 | Berberich et al. |
| 2010/0203573 A1 | 8/2010 | Heinonen et al. |
| 2010/0222196 A1 | 9/2010 | Ito et al. |
| 2010/0300831 A1 | 12/2010 | Pedrazzini |
| 2011/0020948 A1 | 1/2011 | Yamato et al. |
| 2011/0070126 A1 | 3/2011 | Galiano |
| 2011/0076780 A1 | 3/2011 | Yamato et al. |
| 2011/0104742 A1 | 5/2011 | Fox et al. |
| 2011/0123397 A1 | 5/2011 | Yamato et al. |
| 2013/0065797 A1* | 3/2013 | Silbert ............... G01N 35/0099 506/39 |

FOREIGN PATENT DOCUMENTS

| | | |
|---|---|---|
| EP | 0 629 858 A1 | 12/1994 |
| EP | 0 675 195 A1 | 10/1995 |
| EP | 0 895 088 A2 | 2/1999 |
| FR | 2071306 A5 | 9/1971 |
| GB | 2207652 A | 2/1989 |
| GB | 2404735 A | 2/2005 |
| WO | 93/15407 A1 | 8/1993 |
| WO | 95/00244 A1 | 1/1995 |
| WO | 2008/123594 A2 | 10/2008 |
| WO | 2008123882 A1 | 10/2008 |
| WO | 2008/140969 A1 | 11/2008 |
| WO | 2009/152569 A1 | 12/2009 |
| WO | 2010/036829 A1 | 4/2010 |

\* cited by examiner

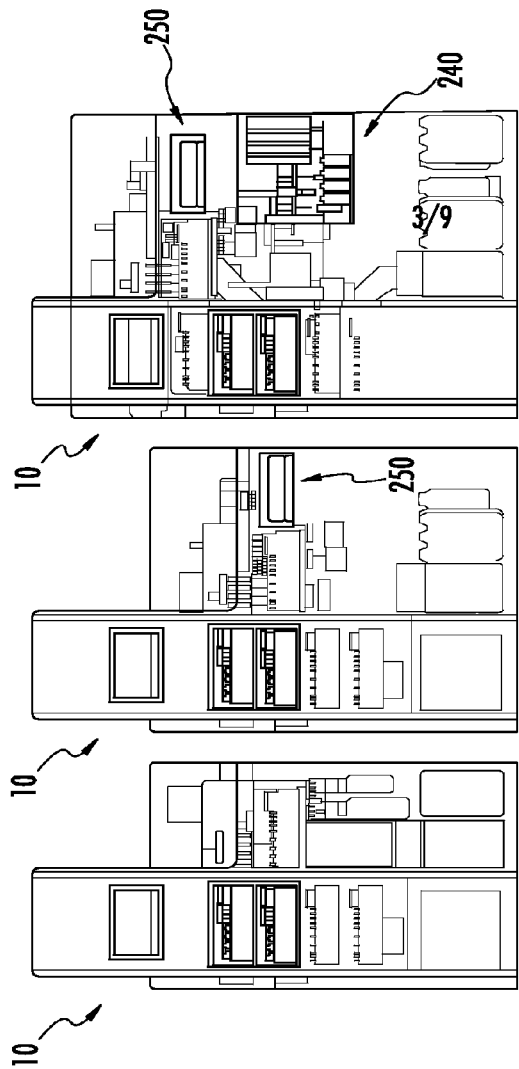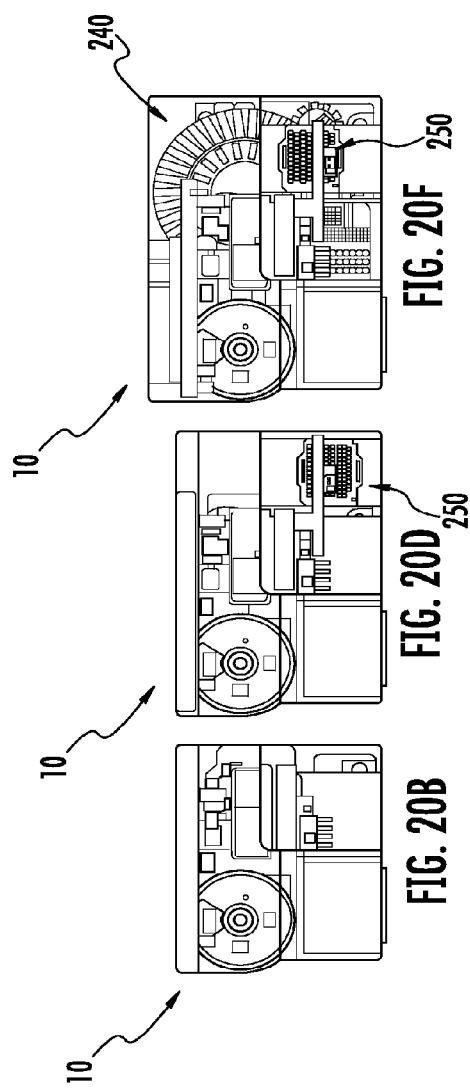

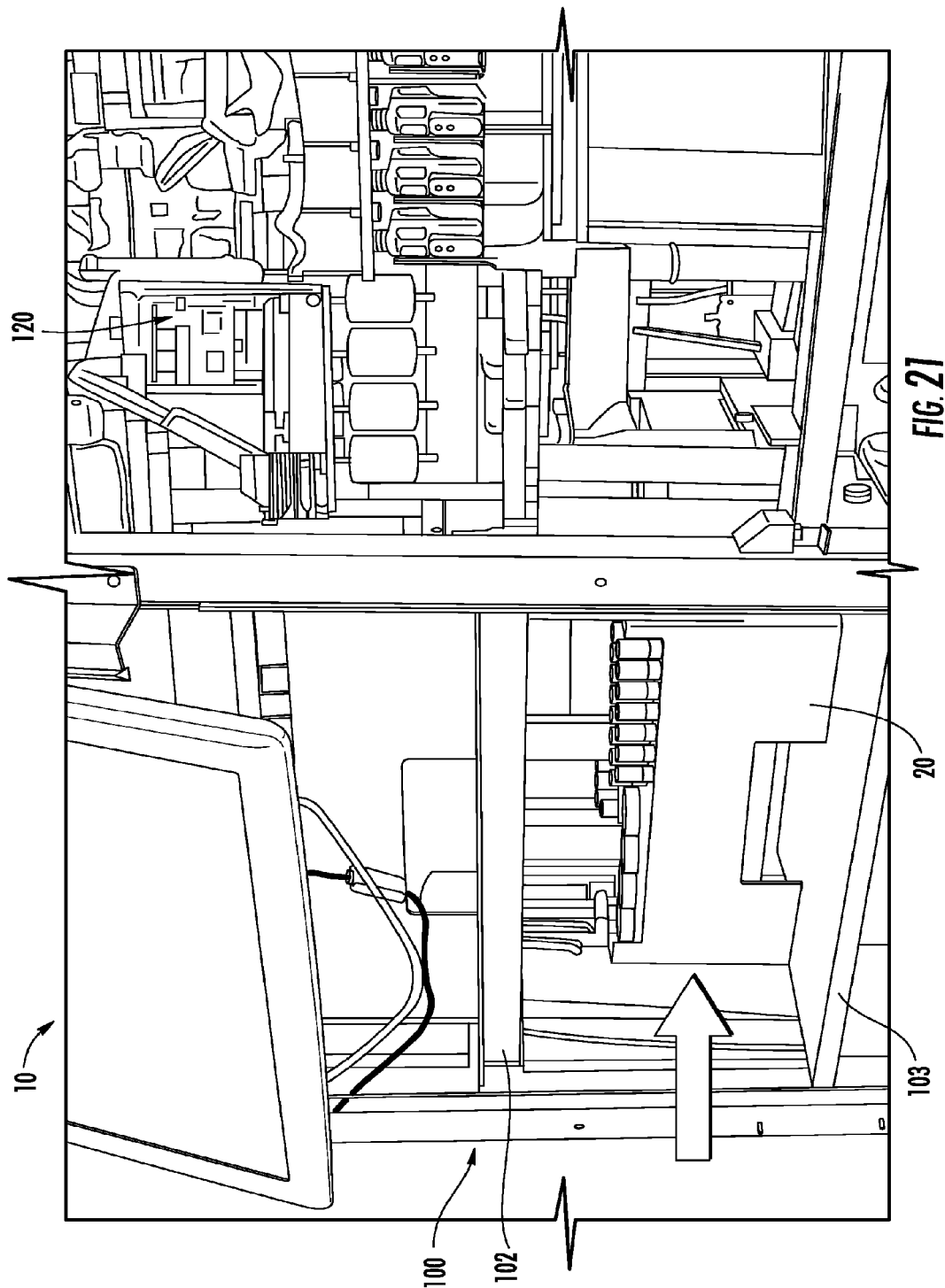

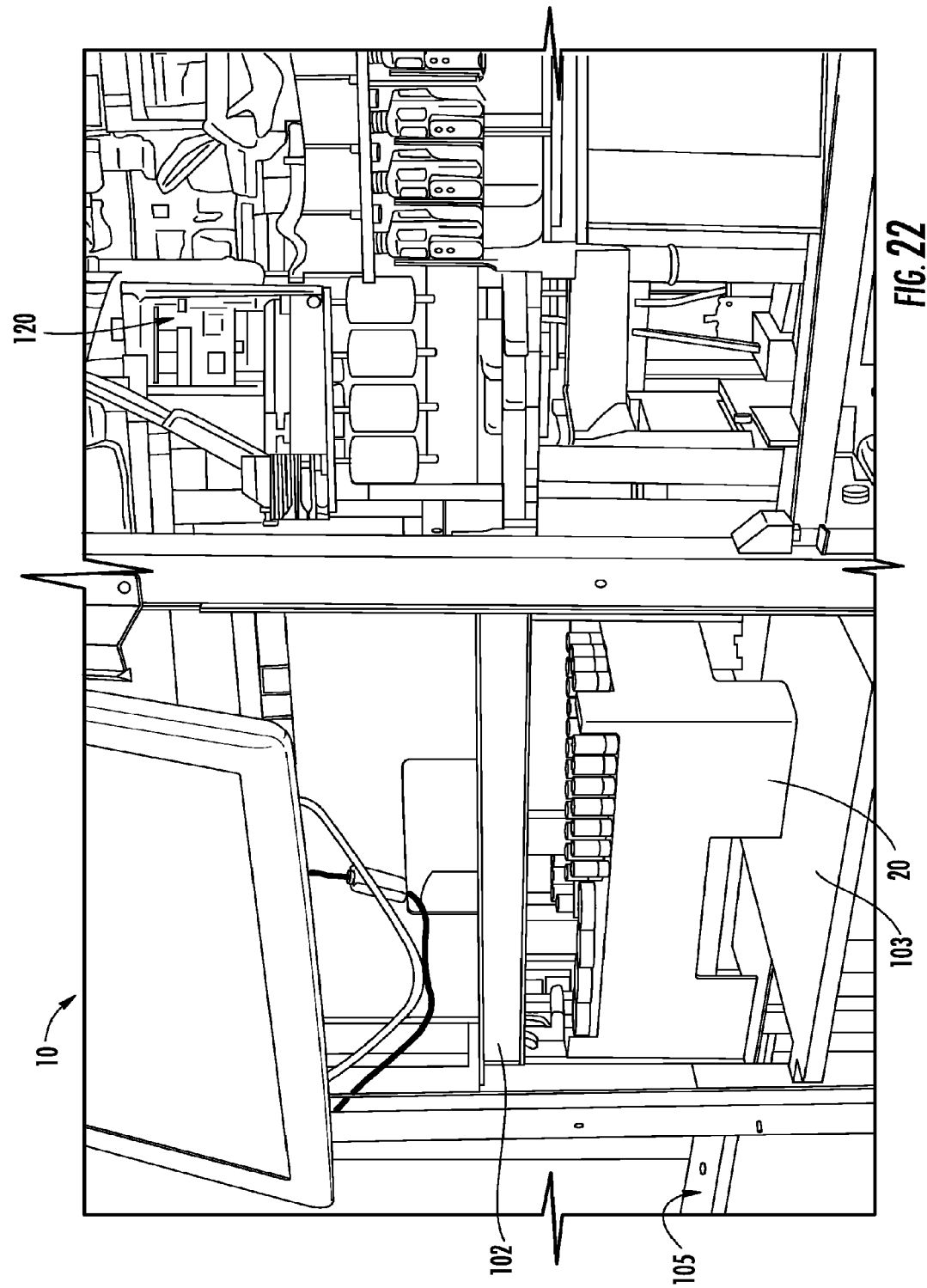

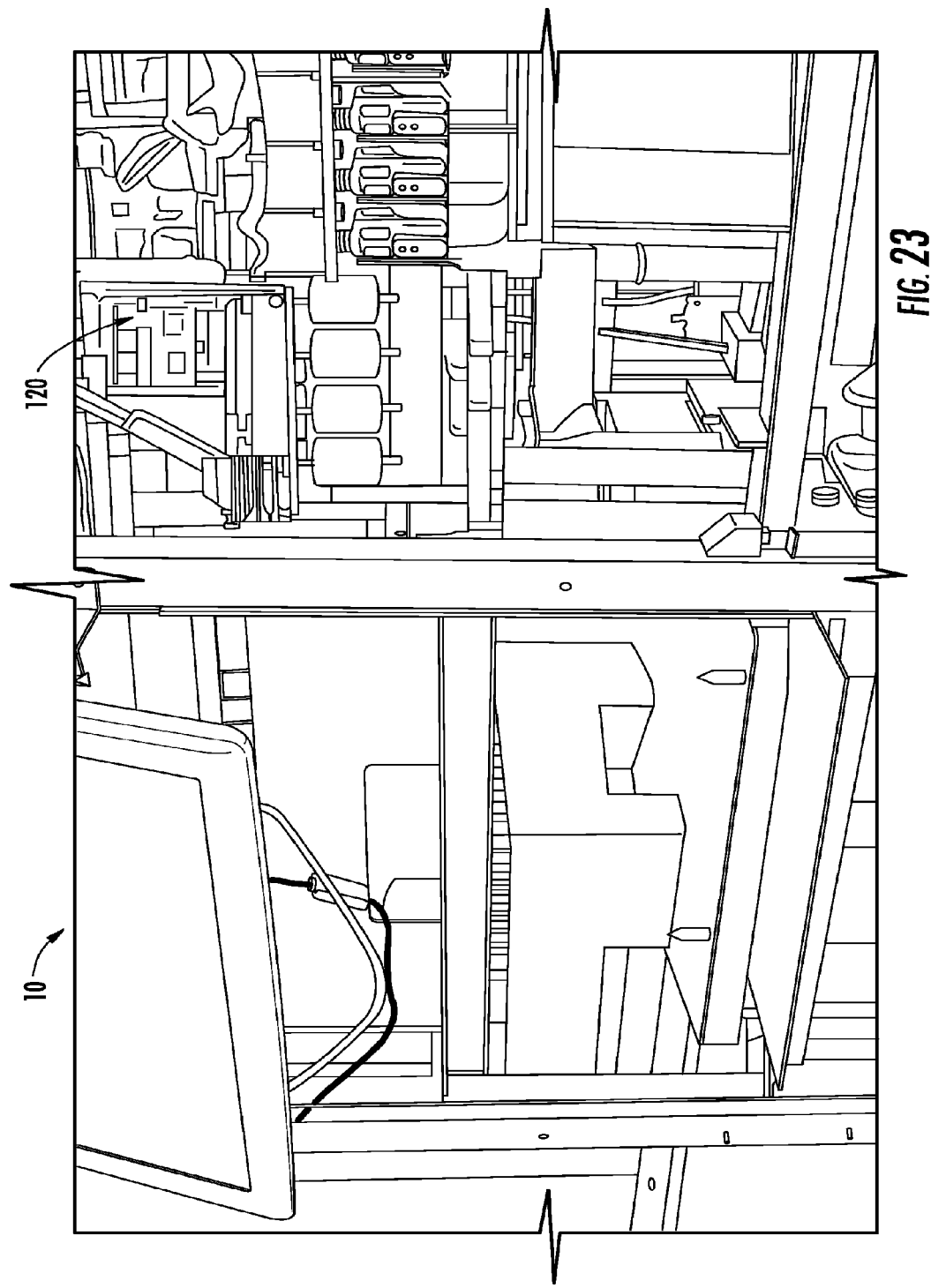

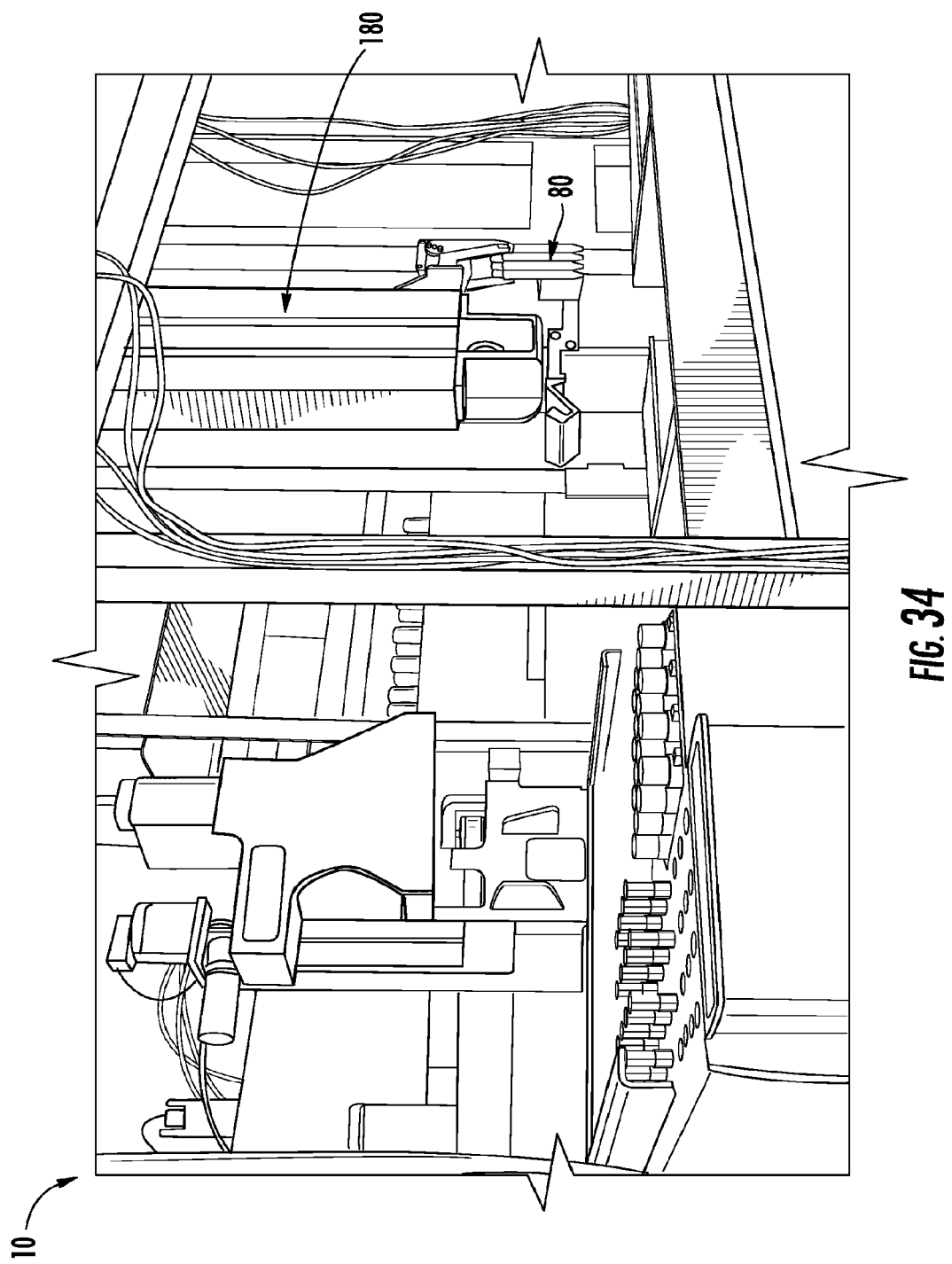

SYSTEM AND METHOD FOR AUTOMATED SAMPLE PREPARATION

CROSS-REFERENCE TO RELATED APPLICATIONS

The present application is a divisional of U.S. patent application Ser. No. 13/672,302 filed Nov. 8, 2012, which claims the benefit of the filing date of U.S. Provisional Patent Application No. 61/556,994 filed Nov. 8, 2011, the disclosures of which are incorporated herein by reference.

BACKGROUND OF THE INVENTION

Embodiments of the present invention generally relate to automated systems and methods for processing biological specimens, such as purifying and concentrating human cervical cells from a cytology sample vial. Specimen samples are typically processed before additional analysis may be undertaken. Efficient and accurate processing of the biological specimens is needed to effectively test a particular specimen. To ensure accuracy and prevent contamination, human processing may be painstakingly slow and cumbersome. Or, several automated processes may be used but are independently controlled and require manual intervention. As such, a need exists for a system and a method for efficiently and accurately processing a plurality of specimen samples at a greater speed.

BRIEF SUMMARY OF THE INVENTION

Various embodiments of the present invention are directed to a system and method for providing automated processing of a biological specimen. The system may include an elevator comprising a plurality of shelves configured to receive a plurality of sample trays. In some embodiments, each of the trays may comprise a plurality of sample containers containing a sample and having a plurality of respective caps engaged therewith and a plurality of centrifuge tube racks each containing a plurality of centrifuge tubes. The system may further include a first transport mechanism configured to transport the trays from the elevator to a processing deck. In some embodiments, the system may include a second transport mechanism coupled to the processing deck and configured to transport the processing deck from the elevator to a first processing location and between the first processing location and a second processing location. According to some embodiments, the system may further include a chain-of-custody device configured to read an identifier on each of the sample containers and a de-capping device configured to remove a plurality of caps from a plurality of respective sample containers. In some embodiments, the system may comprise a pipetting device configured to remove a portion of the sample from each of the de-capped plurality of containers and dispense the removed portion into a plurality of centrifuge tubes. The system may further include a centrifuge device configured to centrifuge a plurality of the centrifuge tubes containing the sample and a third transport mechanism configured to transport each of the centrifuge tube racks from the tray to the centrifuge device.

According to some embodiments, the system may include a sample tray comprising a plurality of molecular tubes having a plurality of respective caps engaged therewith. The system may further include a de-capping device is configured to remove a plurality of caps from the molecular tubes. In some embodiments, the system may include a pipetting device configured to remove a portion of the sample from each of the de-capped plurality of containers and dispense the removed portion into a plurality of de-capped molecular tubes. According to some embodiments, the de-capping device may be configured to remove the plurality of caps while the containers are disposed within the sample tray.

In some embodiments, the system may include a third transport mechanism configured to transport the centrifuge tubes from the centrifuge device to an aspirating and decanting device following a centrifuge operation for aspirating or decanting the centrifuge tubes. The system may include a first transport mechanism configured to engage a bottom surface of each tray and move the tray in both an X-direction and a Z-direction. In some embodiments, the system may further include a second transport mechanism configured to convey the processing deck between the first processing location and the second processing location along a Y-direction. According to some embodiments, the system may include a third transport mechanism configured to transport the plurality of centrifuge tubes from the tray at the second processing location to the centrifuge device in both an X-direction and a Z-direction.

According to some embodiments, the system may include a third transport mechanism configured, after following centrifugation, to transport the plurality of centrifuge tube racks from the centrifuge device to the tray at the second processing location, the second transport mechanism is configured to transport the tray from the second processing location to the first processing location, and the second transport mechanism is configured to transport the tray from the first processing location into the elevator. In some embodiments, the centrifuge tube racks may be disposed within the tray at about an angle of between 13 and 15 degrees.

In some embodiments, the system may include a second transport mechanism configured to transport the processing deck between the first processing location and the second processing location to facilitate access to each of the sample vials and centrifuge tubes with the pipetting device. The system may further include a chain-of-custody device configured to read an identifier on each of the sample containers at the first processing location. In some embodiments, the system may further comprise a second chain-of-custody device configured to read an identifier on each of the trays and centrifuge tube racks in the elevator. The system may include a second chain-of-custody device configured to determine whether each of the sample tubes and centrifuge tube racks are properly positioned within the tray. According to some embodiments, the system may further comprise a third chain-of-custody device configured to read an identifier on each of the centrifuge tubes.

According to some embodiments, the system may include a tray comprising a plurality of disposable syringes, and wherein the pipetting device is configured to engage a plurality of disposable syringes and remove a portion of the sample from each of the de-capped plurality of sample containers with the syringes. The system may further include a pipetting device configured to disengage the plurality of disposable syringes following use. In some embodiments, the system may include a pipetting device configured to mix the sample in each of the de-capped plurality of containers prior to removing the portion of the sample from the sample containers. According to some embodiments, the system may include a de-capping device configured to simultaneously remove a plurality of caps from a plurality of respective sample containers at the first processing location.

In some embodiments, the system may include a pipetting device configured to simultaneously remove a portion of the sample from each of the de-capped plurality of containers and simultaneously dispense the removed portion into a plurality of centrifuge tubes. According to some embodiments, the system may include an elevator comprising a plurality shelves spaced vertically apart from one another, each shelf configured to support at least one of the plurality of trays thereon.

Some embodiments of the present invention may provide for a method for automated sample preparation comprising providing a plurality of trays, each of the trays comprising a plurality of sample containers containing a sample and having a plurality of respective caps engaged therewith, and a plurality of centrifuge tube racks each comprising a plurality of centrifuge tubes. The method may further include automatically transporting the trays to a processing deck and automatically reading an identifier on each of the sample containers. In some embodiments, the method may further comprise automatically removing a plurality of caps from a plurality of respective sample containers. In some embodiments, the method may include automatically removing a portion of the sample from each of the de-capped plurality of containers. According to some embodiments, the method may include automatically dispensing the removed portion into a plurality of centrifuge tubes. In some embodiments, the method may include automatically transporting each of the centrifuge tube racks to a centrifuge device and automatically centrifuging a plurality of the centrifuge tubes containing the sample with the centrifuge device.

Some embodiments of the present invention provide for a method for automated processing comprising providing a plurality of trays, each of the trays comprising a plurality of molecular tubes having a plurality of respective caps engaged therewith. The method may further include automatically removing the plurality of caps from the molecular tubes. In some embodiments, the method may include automatically removing a portion of the sample from each of the de-capped plurality of containers and automatically dispensing the removed portion into a plurality of the de-capped molecular tubes. In some embodiments, the method may include automatically removing a plurality of caps from a plurality of respective sample containers while the containers are disposed within the sample tray.

Some embodiments may provide a method including automatically transporting each of the centrifuge tube racks to an aspirating and decanting device following a centrifuge operation for aspirating and/or decanting the centrifuge tubes. The method may further include automatically transporting the tray with a first transport mechanism configured to engage a bottom surface of the tray and move the tray in both an X-direction and a Z-direction. In some embodiments, the method may include automatically transporting the tray using a second transport mechanism configured to convey a processing deck between a first processing location and a second processing location along a Y-direction. According to some embodiments, the method may further include, upon following centrifugation, automatically transporting the plurality of centrifuge tube racks from the centrifuge device to the tray at a second processing location, automatically transporting the tray from the second processing location to the first processing location and automatically transporting the tray from the first processing location into the elevator.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 20A illustrates a system configured to provide an automated processing of a biological specimen according to some embodiments of the present invention;

FIG. 20B illustrates a top view of the system of FIG. 20A according to some embodiments of the present invention;

FIG. 20C illustrates a system including additional modules configured to engage the system to provide additional automated processing of a biological specimen according to some embodiments of the present invention;

FIG. 20D illustrates a top view of the system of FIG. 20C according to some embodiments of the present invention;

FIG. 20E illustrates a system including additional modules configured to engage the system to provide additional automated processing of a biological specimen according to some embodiments of the present invention;

FIG. 20F illustrates a top view of the system of FIG. 20E according to some embodiments of the present invention;

FIG. 21 illustrates a user loading a sample tray into the system according to some embodiments of the present invention;

FIG. 22 illustrates a system verifying the identity of specimen containers and other disposable components according to some embodiments of the present invention;

FIG. 23 illustrates a first transport mechanism moving a sample tray according to some embodiments of the present invention;

FIG. 34 illustrates a third transport mechanism transporting a centrifuge tube rack according to yet another embodiment of the present invention.

DETAILED DESCRIPTION

The present invention will now be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout. The terms top, bottom, side, up, down, upwards, downwards, vertical, horizontal, front, rear, and the like, to the extent used herein, do not imply a required limitation in all embodiments of the present invention, but rather are used herein to help describe relative direction and/or orientation in the example embodiments illustrated in the figures.

Various embodiments of the present invention generally provide for a system for automated processing of a biological sample. For example, the system may be configured to automate all of the steps involved in preparing a cell pellet, including automated handling and transport, chain-of-custody verification, de-capping/capping of sample vials and/or tubes, pipetting, centrifugation, aspiration, and/or decanting. In some embodiments, the system may include additional modules for providing additional automated processes, such as preparation of a sample slide via a downstream slide deposition and staining module. According to some embodiments, the system may be configured to dispense sample fluid from a sample vial to a transport tube for performing molecular testing. The system may include computer controlled robotics that perform all of the necessary operations to prepare a specimen for further downstream processing and analysis, such as using PrepStain™ slide processing (Tripath Imaging), Viper™ HT/LT Systems (Becton Dickinson), and/or FocalPoint™ slide analysis (Tripath Imaging), for cytological, imaging, and/or molecular testing. Further still, some embodiments of the present invention provide for a method of automated processing of a specimen sample for further downstream processing and analysis.

Figure 1:
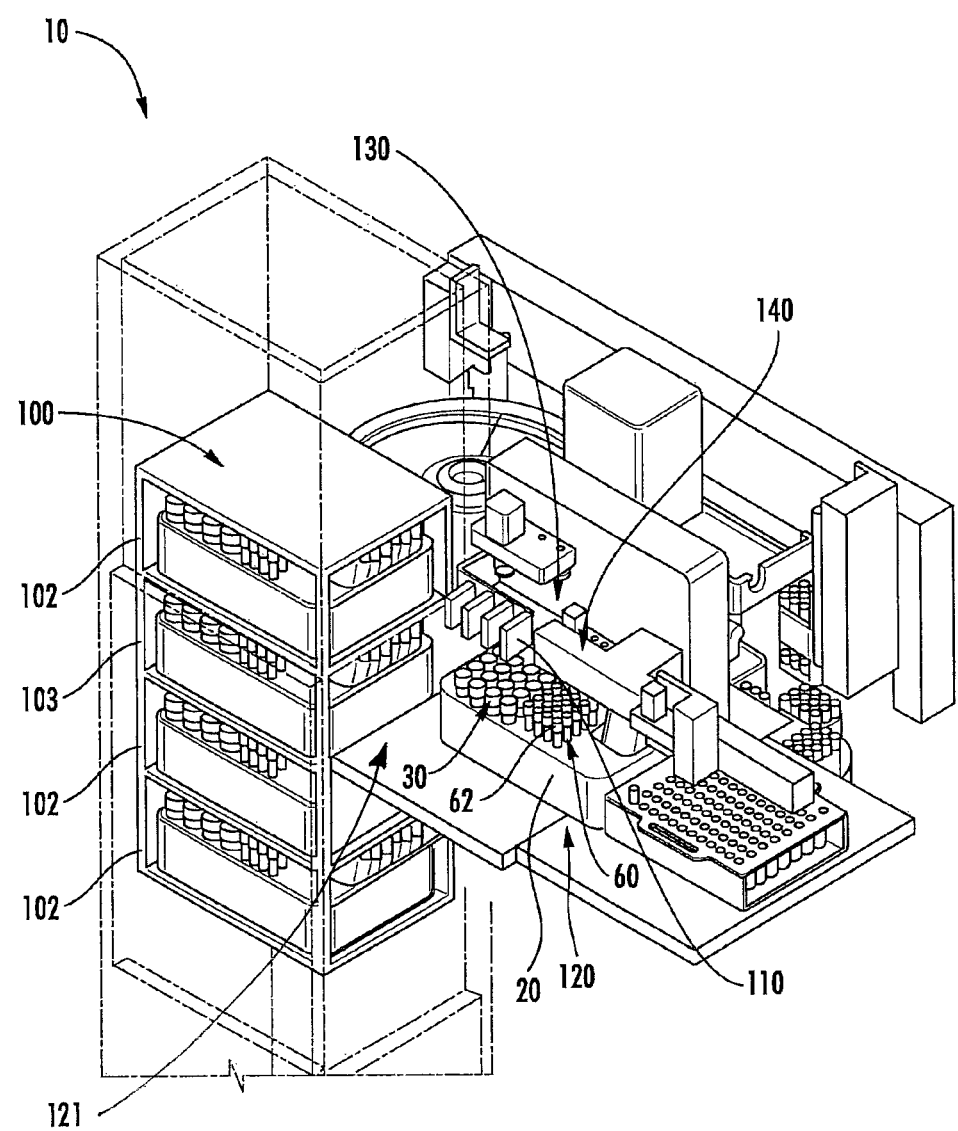
FIG. 1 illustrates a system configured to automatically process a biological specimen according to some embodiments of the present invention.
Figure 2:
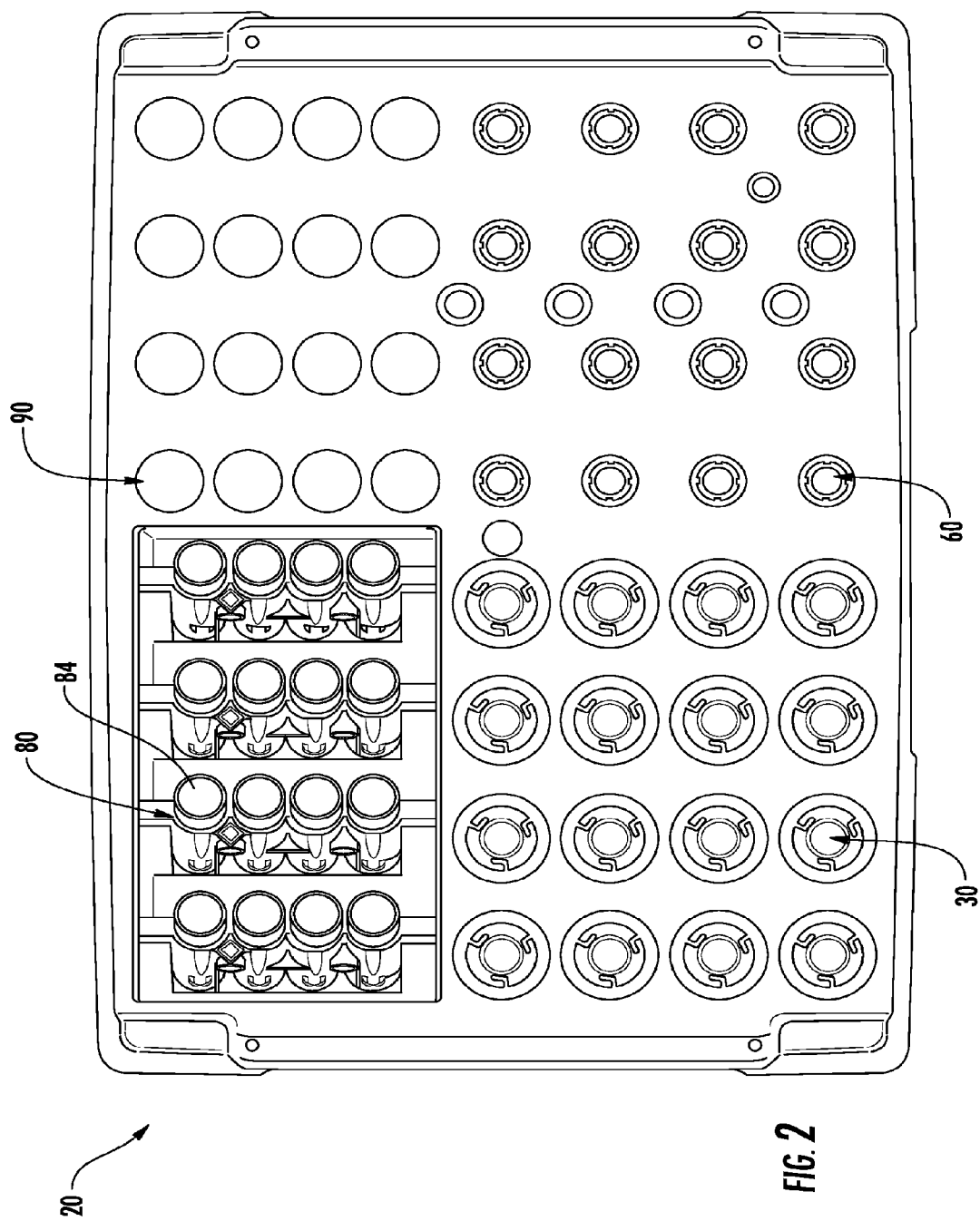
FIG. 2 illustrates a sample tray according to some embodiments of the present invention.
Figure 3:
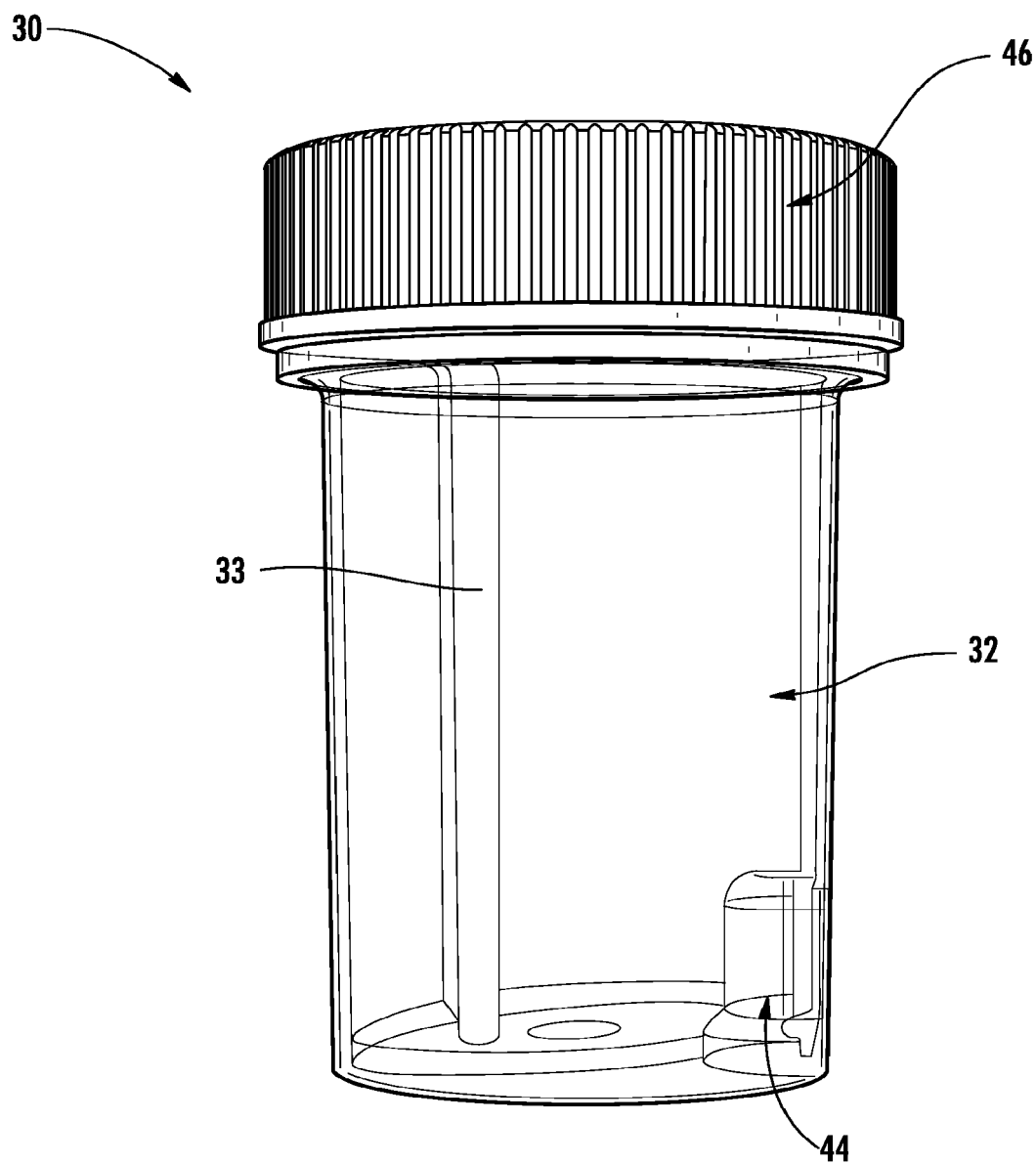
FIG. 3 illustrates a specimen container configured to store a biological specimen according to some embodiments of the present invention.
Figure 7:
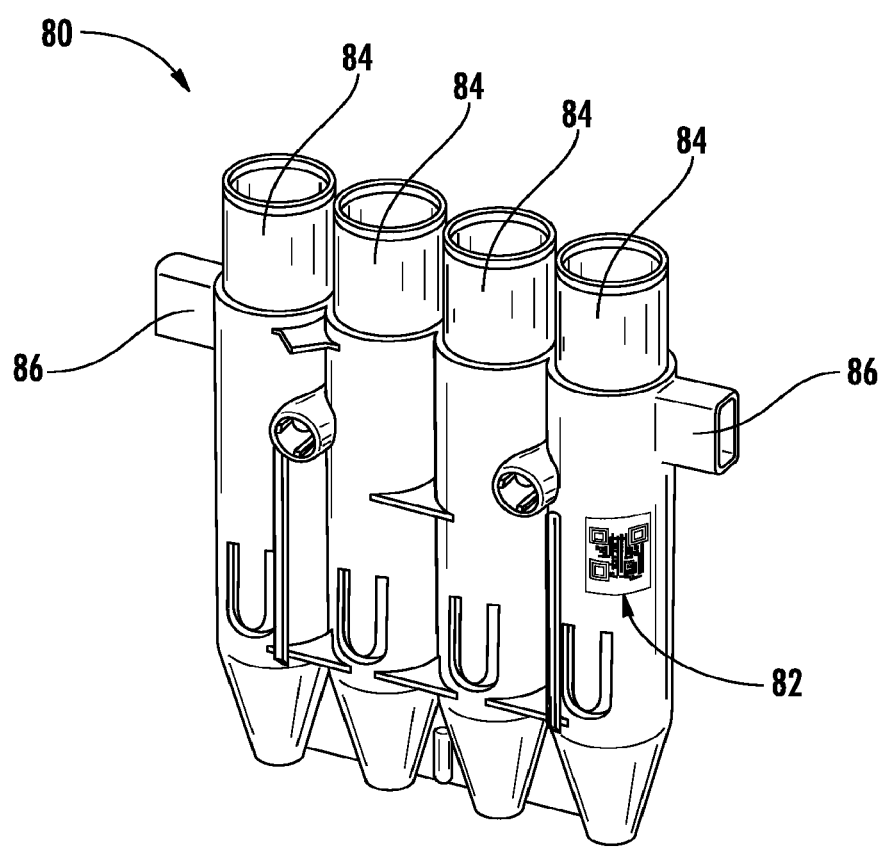
FIG. 7 illustrates a centrifuge tube rack according to some embodiments of the present invention.
Figure 8:
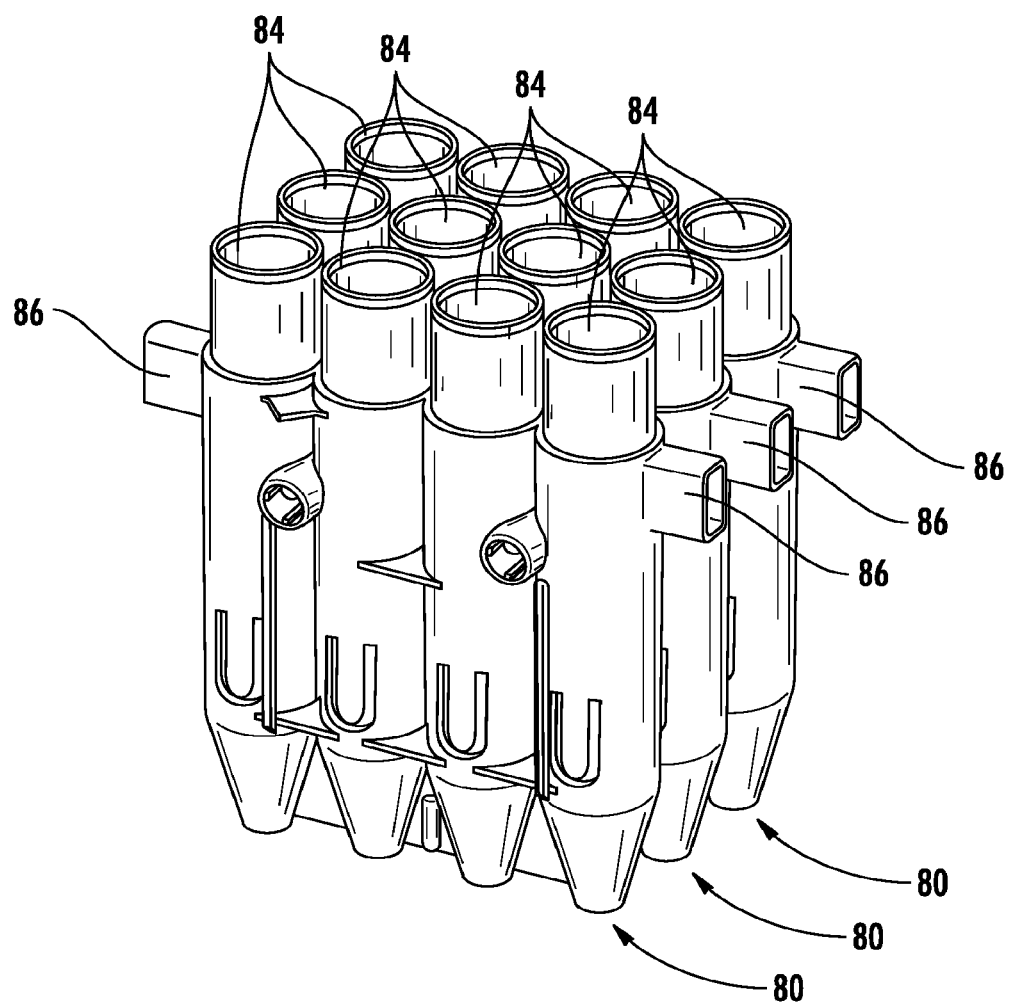
FIG. 8 illustrates a plurality of centrifuge tube racks according to some embodiments of the present invention.

As shown in FIG. 1, the system 10 may include a plurality of sample trays 20 for storing, receiving, and/or processing a biological specimen. In some embodiments of the present invention, a sample tray 20 may be configured to receive at least one specimen container 30, at least one centrifuge tube rack 80, at least one molecular tube 60, and/or at least one pipetting or aspirating device, such as a syringe 90, as shown in FIG. 2. In addition, the centrifuge tube rack 80 may be configured to receive at least one centrifuge tube 84 therein. As shown in FIG. 7, the centrifuge tube rack 80 may receive four centrifuge tubes 84 therein. According to some embodiments, the sample tray may be configured to receive sixteen specimen containers 30, sixteen molecular tubes 60, four centrifuge tube racks 80, wherein each centrifuge tube rack comprises four centrifuge tubes 84, and/or sixteen syringes 90. As such, each sample tray 20 is configured to provide for the processing of sixteen distinct specimens, as each molecular tube 60, centrifuge tube 84, and/or syringe 90 corresponds to a distinct specimen stored within a specimen container 30. However, any number of specimen containers 30, molecular tubes 60, and centrifuge tube racks 80 may be employed with the sample tray 20. In addition, the specimen container 30 may include a specimen vial 32 and a specimen container cap 46, wherein the specimen vial and specimen container cap are configured to engage one another to create a sealed and closed environment to prevent the contamination of the specimen. Further, the molecular tube 60 may include a molecular tube cap 62, wherein the molecular tube and molecular tube cap are configured to engage one another to create a sealed and closed environment to prevent contamination of the specimen for storage and/or downstream processing.

In some embodiments, the specimen container 30 may include a specimen vial 32 and a specimen container cap 46, as shown in FIGS. 3-6. The specimen container 30 may include features configured to provide for efficient and automated processing of the specimen stored therein. As described in U.S. Provisional Patent Application No. 61/557,011 filed on Nov. 8, 2011 and U.S. Patent application entitled "Container and Cap for Biological Specimen" filed concurrently herewith, both of which are incorporated herein in their entirety by reference, a specimen container 30 may include a tower 33 therein, wherein the tower defines a separate first chamber 36 and a second chamber 38. The first chamber 36 and second chamber 38 may be in fluid communication with one another. In addition, the specimen container 30 may include an insert 39 therein that defines a first opening 40 and a second opening 42. The first opening 40 may provide access to the first chamber 36, while the second opening 42 provides access to the second chamber 38. The second opening 42 may be configured to receive a specimen therein prior to placing the specimen container 30 within the sample tray 20. In addition, the first opening 40 may be configured to receive a syringe 90 therethrough such that the syringe may mix and/or aspirate the specimen stored within the first chamber 36 of the specimen container 30. Further, the specimen container 30 may include a specimen container cap 46 configured to engage the specimen vial 32 such that when the specimen container cap is engaged with the specimen vial, the specimen container cap and specimen vial create a sealed and closed environment to prevent contamination of a specimen stored therein.

As previously mentioned, some embodiments include a sample tray 10 configured to receive a plurality of centrifuge tube racks 80, such as at least four centrifuge tube racks 80. Each of the centrifuge tube racks 80, as shown in FIG. 7, may be configured to receive a plurality of centrifuge tubes 84 therein, such as at least four centrifuge tubes 84 therein. According to some embodiments, the sample tray 20 may be configured to store the plurality of centrifuge tube racks 80 at an angle offset from the vertical axis of the sample tray 20, as shown in FIGS. 17A-17D. As such, the centrifuge tubes 84 positioned within the centrifuge tube racks 80 are also disposed at an angle offset from the vertical axis of the sample tray 20. Accordingly, the offset centrifuge tubes 84 may advantageously provide for the prevention of disrupting the surface tension of materials disposed within the centrifuge tube. For example, prior to dispensing a specimen sample within the centrifuge tube 84, a density reagent may be dispensed into the centrifuge tube, wherein the density reagent has a greater density than the specimen sample. As such, when the specimen sample is dispensed into a centrifuge tube 84 containing the density reagent, the specimen sample will be dispensed along an interior surface of the centrifuge tube such that the surface tension of the density reagent is not disrupted.

Figure 9:
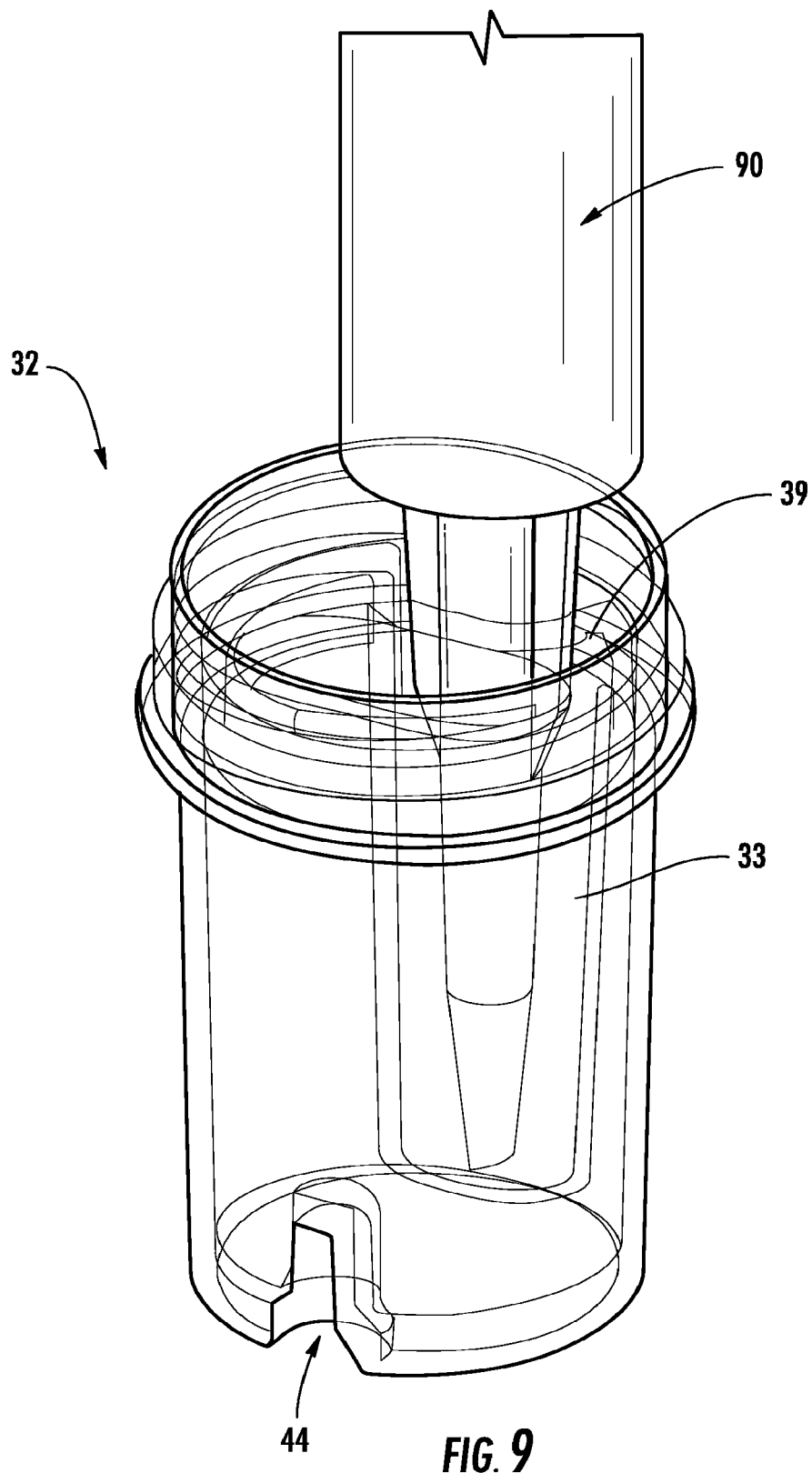
FIG. 9 illustrates a syringe and a specimen container according to some embodiments of the present invention.

In addition, the sample tray 20 may further include a plurality of syringes 90. In some embodiments, the user may load the disposable syringes 90 into the sample tray 20 before placing the sample tray into the system 10 for automated processing. According to one embodiment, the syringes 90 may be 12 ml disposable syringes. The syringe 90 may further include a narrowed section at the syringe tip opening, which provides for shearing the specimen sample fluid. According to some embodiments, the syringe 90 may be inserted into a specimen container 30 to aspirate at least a portion of the specimen sample. In some embodiments, prior to aspirating the specimen for processing, the syringe 90 may be lowered into the specimen container 30, as shown in FIG. 9, and may mix the specimen sample fluid by aspirating and then dispensing the specimen sample fluid multiple times while the syringe remains positioned within the specimen container. As such, the narrowed section of the syringe tip opening may shear the specimen sample fluid during the repeated aspiration and dispensing step.

According to some embodiments, the system 10 may further include a tray handling elevator 100, as shown in FIG. 1. In some embodiments, the tray handling elevator 100 may include a plurality of shelves 102, wherein each shelf is configured to receive and/or store at least one sample tray 20. In addition, the elevator 100 may include an input shelf 103 configured to receive a sample tray 20 prepared by a user. The input shelf 103 may be accessible by a user via a door, wherein the remaining plurality of shelves 102 of the tray handling elevator are not accessible from outside of the system 10. Accordingly, once a sample tray 20 is loaded within the system 10 via the input shelf 103, the sample tray 20 may be safely stored within the tray elevator 100 on any one of the plurality of shelves 102.

Figure 19:
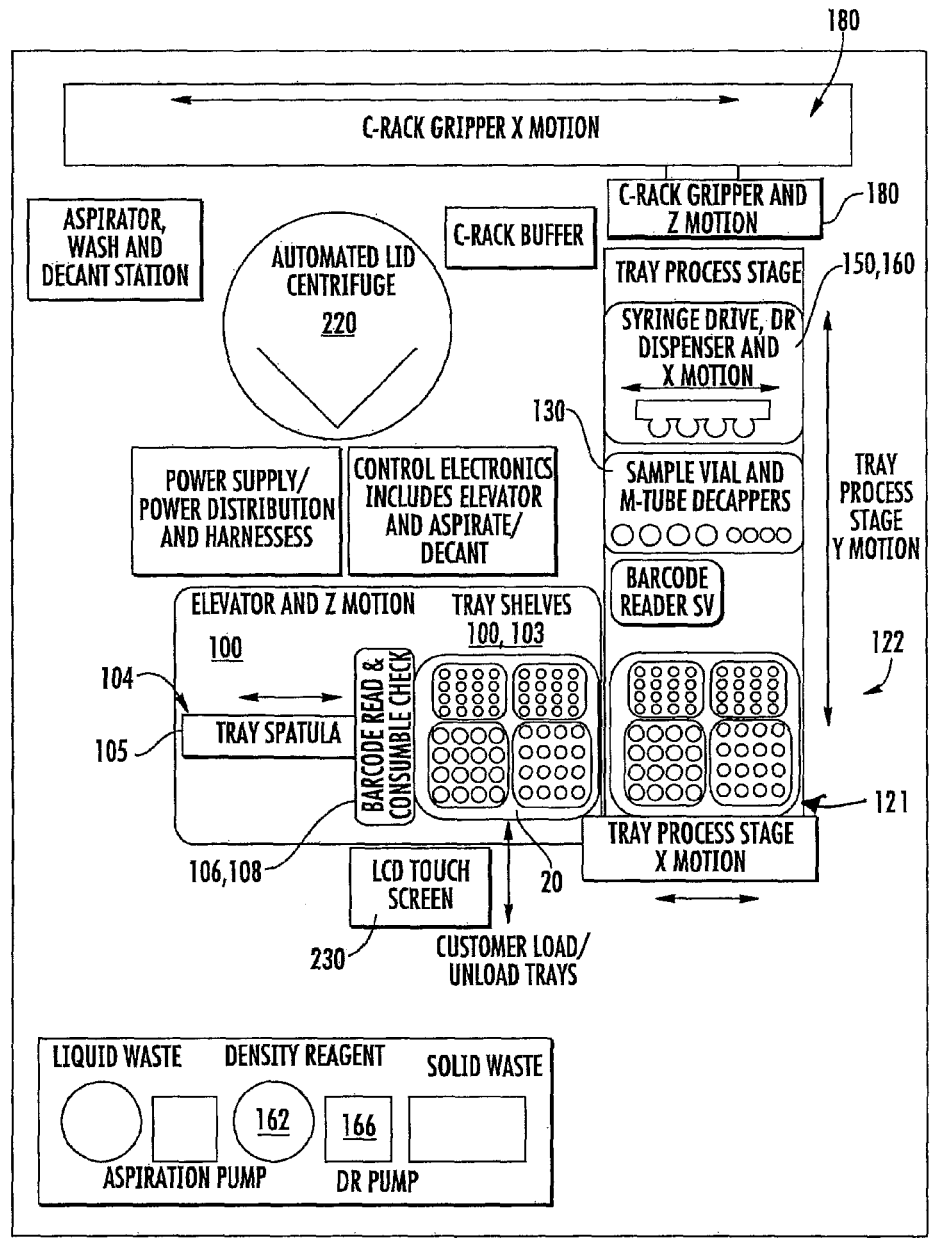
FIG. 19 illustrates a system block diagram of a system for automatically processing a biological specimen according to some embodiments of the present invention.

In addition, the system may include a first transport mechanism 105 configured to move in the X-axis and the Z-axis direction. For example, the first transport mechanism 105 may include a spatula 104, as shown in FIG. 19, configured to move between any one of the elevator shelves 102. According to some embodiments, the spatula 104 may be configured to engage a sample tray 20. In some embodiments, the spatula 104 may include an engagement feature, such as a spatula receptacle configured to engage a tray pin defined in a bottom surface of the sample tray 20. As such, the spatula 104 may be configured to engage and secure a tray 20 disposed on the input shelf and/or move the tray to any one of the plurality of shelves 102. Likewise, the spatula 104 may be configured to return the tray 20 to the input shelf 103 for removal from the system. In addition, it is understood that the first transport mechanism 104 may utilize any engagement mechanism to engage the tray 20 at any desired location on the tray to facilitate transport of the tray, such as with a gripping device.

In some embodiments, the system 10 may include a plurality of identification and/or verification devices. For example, the elevator 100 may include a first chain-of-custody or imaging device 106 configured to verify that the plurality of disposables, such as the specimen containers, centrifuge tube racks, centrifuge tubes, molecular tubes and/or syringes, are properly seated within the sample tray. According to some embodiments, the first imaging device 106 may use machine vision software to compare the height of the disposables to a reference target located within the elevator. In addition, the first imaging device 106 may be configured to read identification indicia, such as a sample tray identification indicia 22, a centrifuge tube rack identification indicia 82 and/or the like. According to some embodiments, the elevator 100 may include a second chain-of-custody or imaging device 108 configured to verify the identity of the plurality of disposables housed within the sample tray 20. For example, the second imaging device 108 may be configured to read identification indicia, such as a molecular tube identification indicia 64, a centrifuge tube identification indicia 85 and/or the like. In some embodiments, the system 10 may include a third imaging device 110. For example, a specimen container de-capping device 130 may include a third chain-of-custody or imaging device 110 configured to read identification indicia, such as a specimen container identification indicia 34. According to some embodiments, any one of the identification indicia may include a one-dimensional barcode, a two-dimensional barcode and/or any unique visual identifier. In some embodiments, the identification indicia may include a label that includes a tear-off portion. The label may further include the unique visual identifier, such as the two-dimensional barcode. In some embodiments, the tear-off portion may include identifying information that corresponds to the identifying information on the label remaining on the specimen container, the centrifuge tube, and/or the molecular tube.

Figure 10:
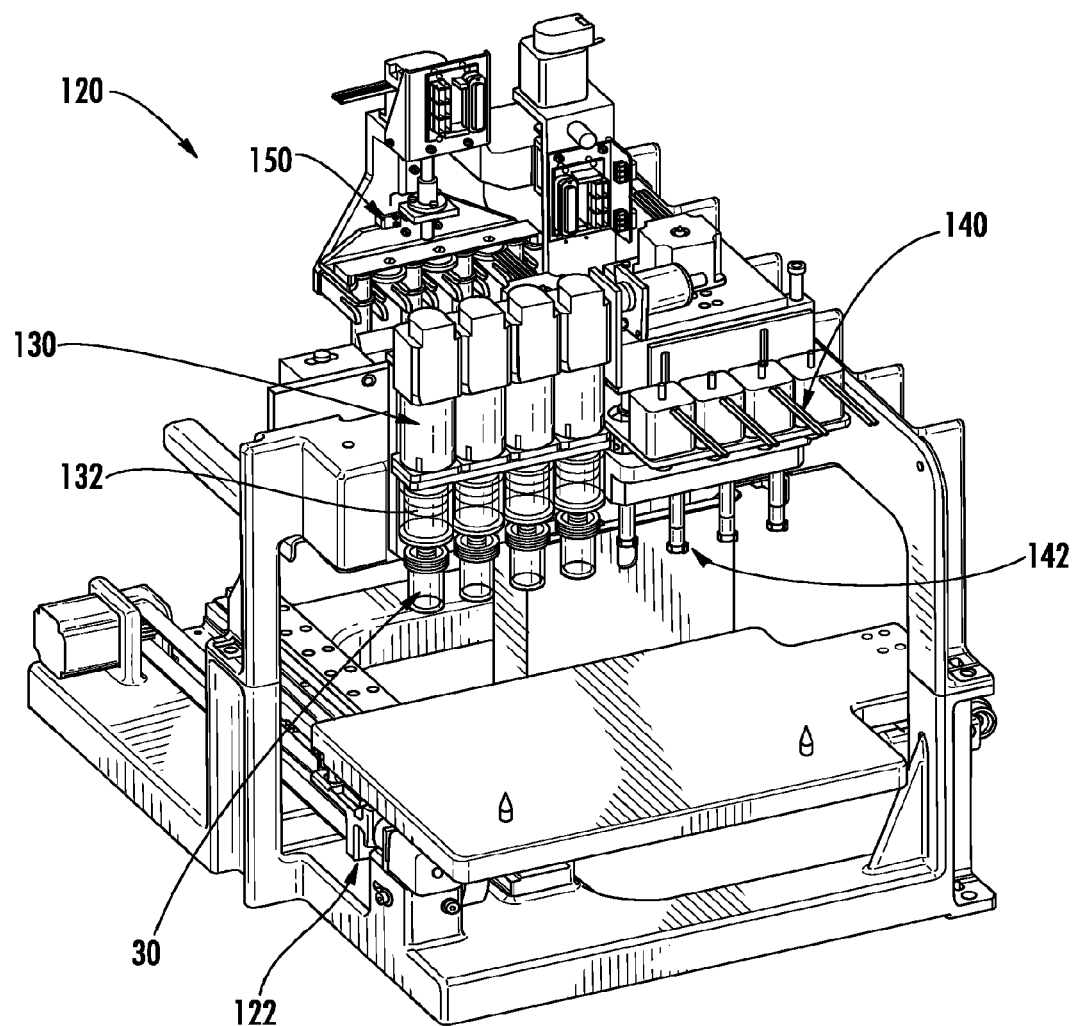
FIG. 10 illustrates a processing device according to some embodiments of the present invention.
Figure 11:
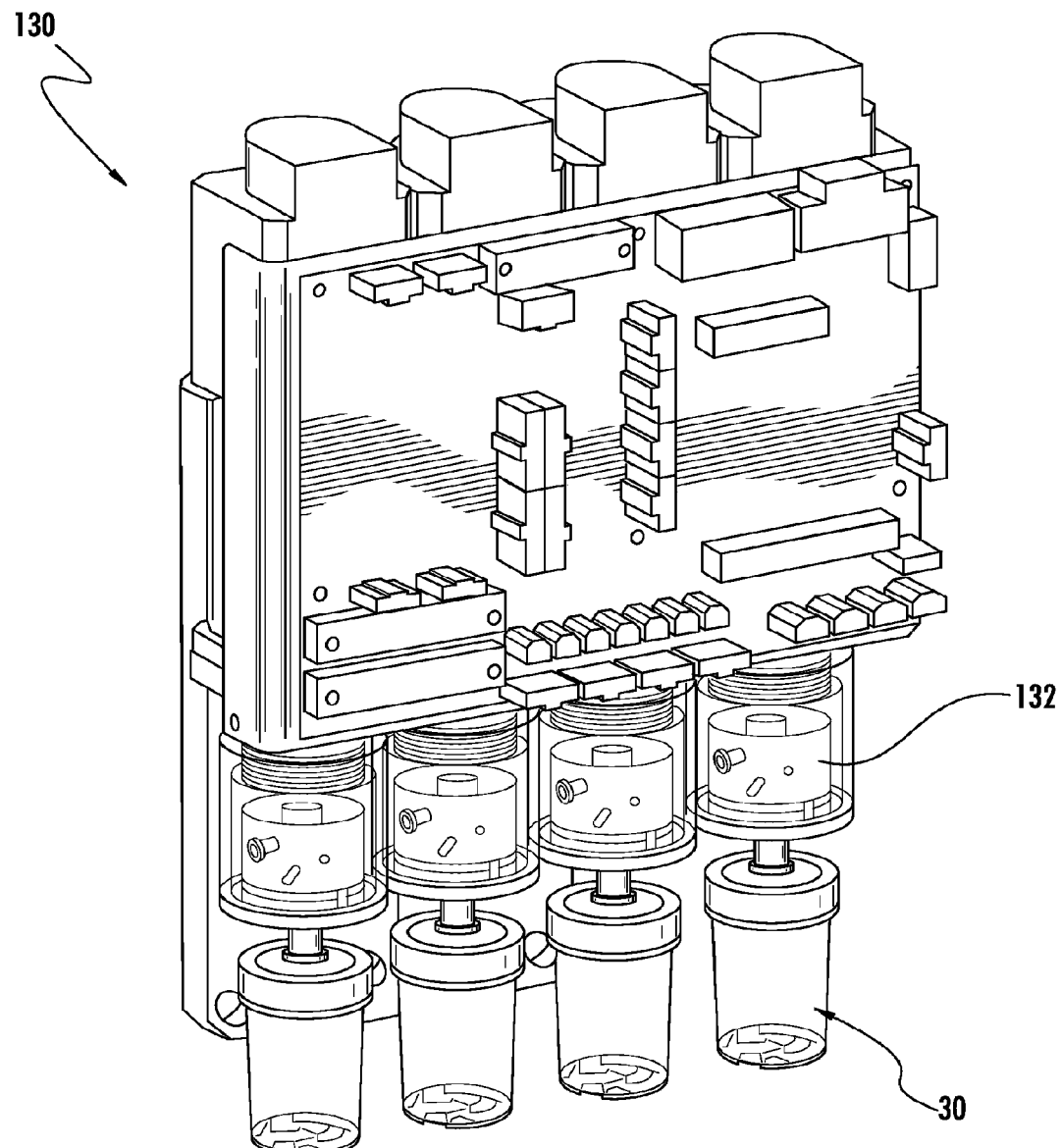
FIG. 11 illustrates a de-capping device according to some embodiments of the present invention.
Figure 12:
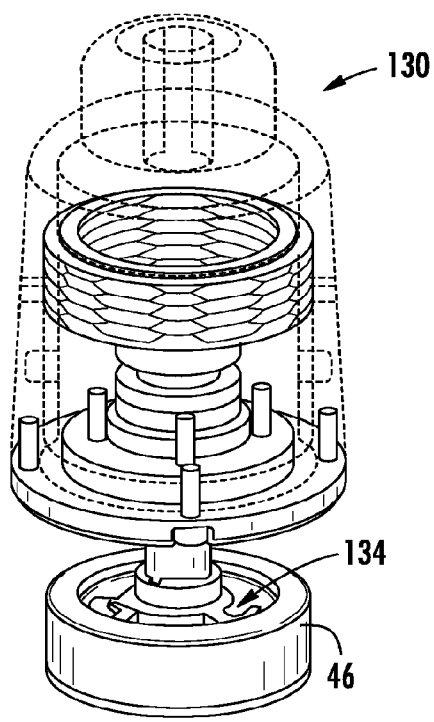
FIG. 12 illustrates a capper/decapper mechanism according to some embodiments of the present invention.
Figure 13A:
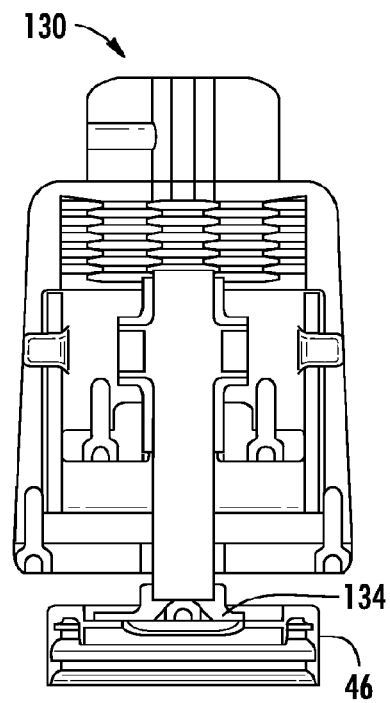
FIG. 13A illustrates a cross-sectional view of a capper/decapper mechanism according to some embodiments of the present invention.
Figure 13B:
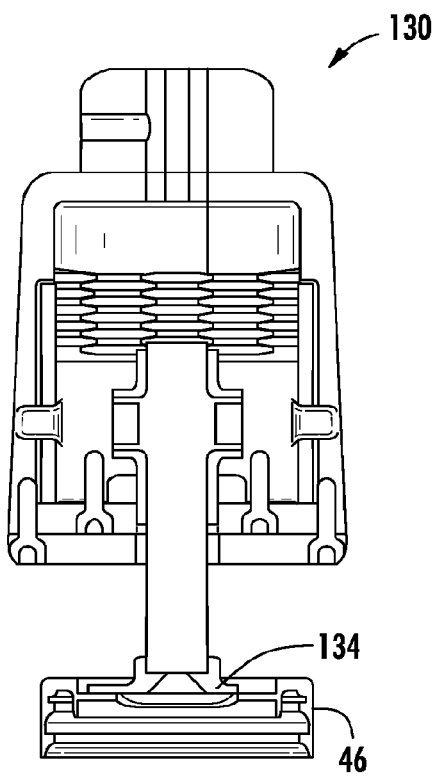
FIG. 13B illustrates a cross-sectional view of a capper/decapper mechanism according to some embodiments of the present invention.

In some embodiments, the system 10 may include a processing station 120 configured to engage the plurality of specimen containers 30, centrifuge racks 80, centrifuge tubes 84, molecular tubes 60, and/or syringes 90 housed within the sample tray 20, as shown in FIG. 10. The processing station 120 may include a specimen container de-capping device 130. The specimen container de-capping device 130, as shown in FIG. 11, may include a plurality of capper/decapper mechanisms 132. The container capper/decapper mechanism 132 may be configured to engage the specimen container cap 46 and remove the cap from the specimen vial 32, as shown in FIGS. 13A-13B. According to one embodiment, the specimen container de-capping device 130 may include a plurality of capper/decapper mechanisms 132 that correspond to a number of specimen containers 30 disposed along a row within the sample tray 20. For example, the specimen container de-capping device 130 may include four capper/decapper mechanisms 132 that correspond to four specimen containers 30 that are disposed along a first row of specimen containers within the sample tray 20.

Figure 14:
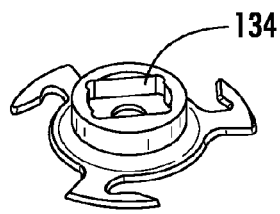
FIG. 14 illustrates a capper/decapper engagement mechanism according to some embodiments of the present invention.
Figure 15:
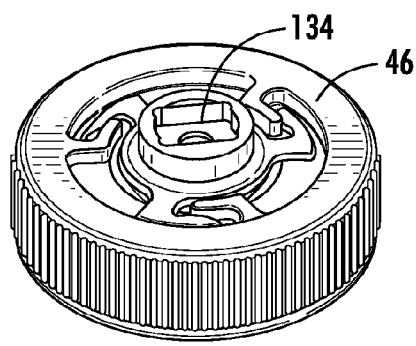
FIG. 15 illustrates a capper/decapper engagement mechanism engaged with a specimen container cap according to some embodiments of the present invention.

According to one embodiment, the container capper/decapper mechanism 132 may include a tri-star head 134 configured to engage the specimen container cap 46, as shown in FIG. 15. Although the tri-star head 134, as shown in FIG. 14, includes three chuck fingers 136, one of ordinary skill in the art may appreciate that the tri-star head 134 may include any number of chuck fingers 136 equal to the number of cap fingers 48 of the container cap 46. In some embodiments, the container capper/decapper mechanism 132 may be configured to move the tri-star head 134 vertically along a vertical axis of a specimen container 30. For example, the container capper/decapper mechanism 132 may be configured to move the tri-star head 134 approximately 10 mm in the vertical direction. As such, the container capper/decapper mechanism 132 may be configured to lower the tri-star head 134 onto the container cap 46. In some embodiments, the container capper/decapper mechanism 132 may also be configured to rotate the tri-star head 134 to engage the cap fingers 48.

Figure 4:
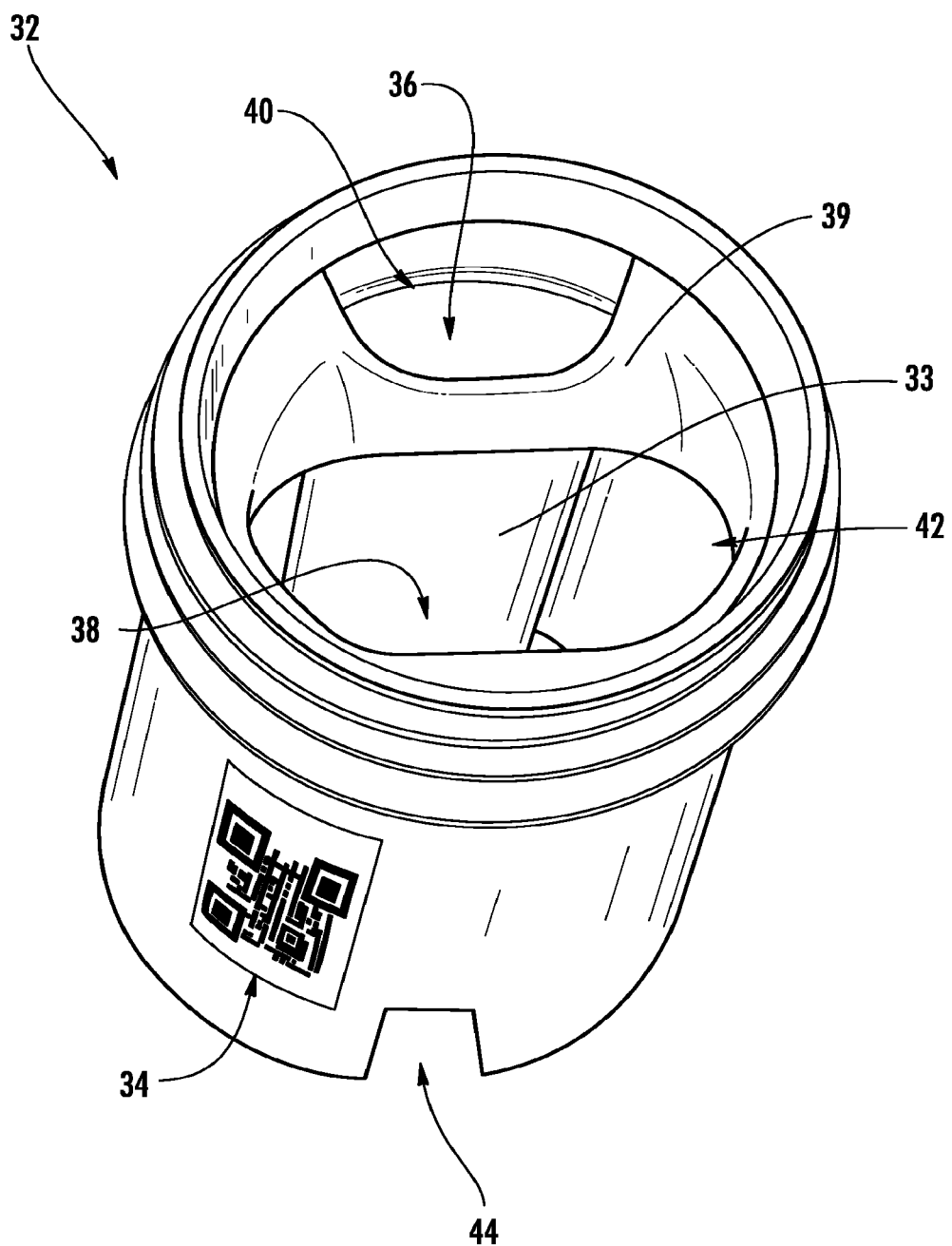
FIG. 4 illustrates a vial of a specimen container configured to store a biological specimen according to some embodiments of the present invention.
Figure 5:
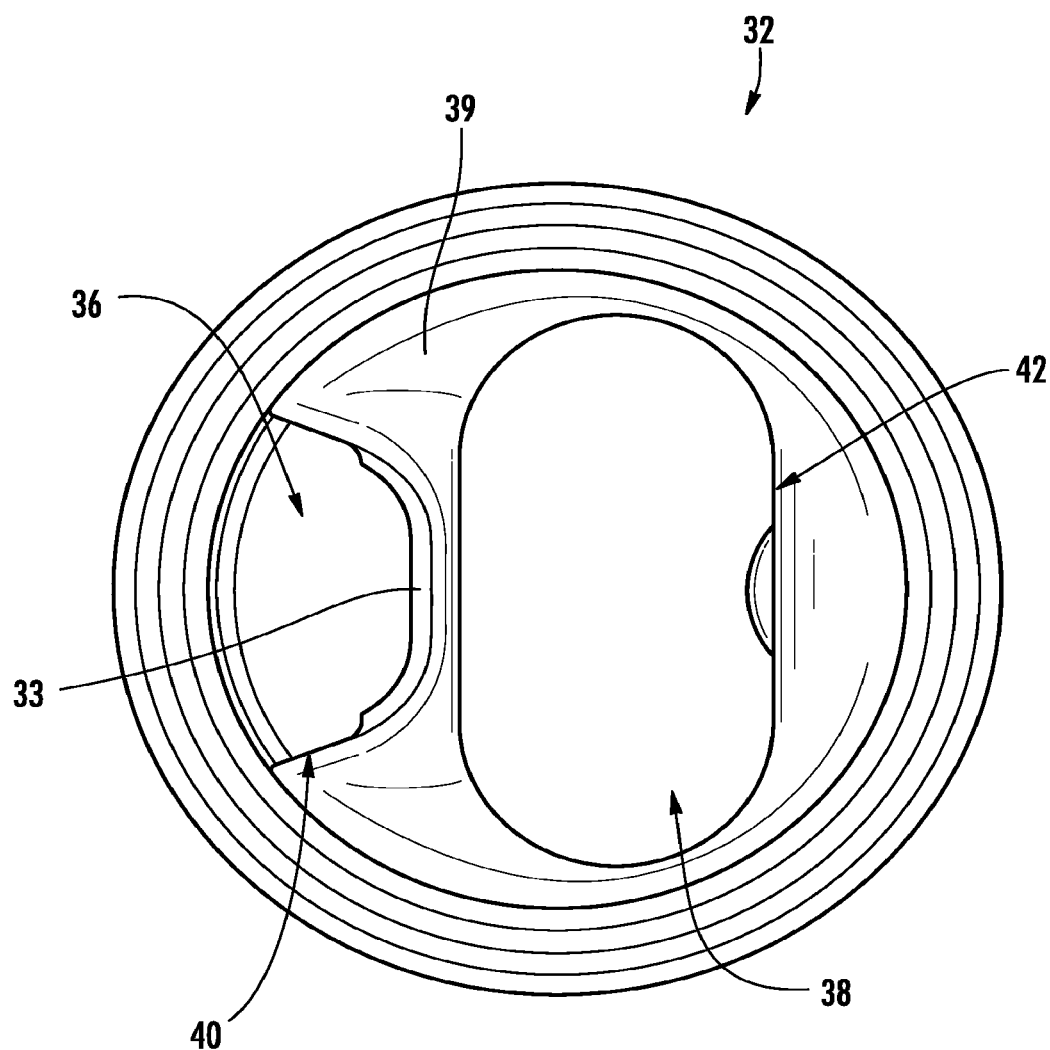
FIG. 5 illustrates a top view of the vial according to some embodiments of the present invention.
Figure 6:
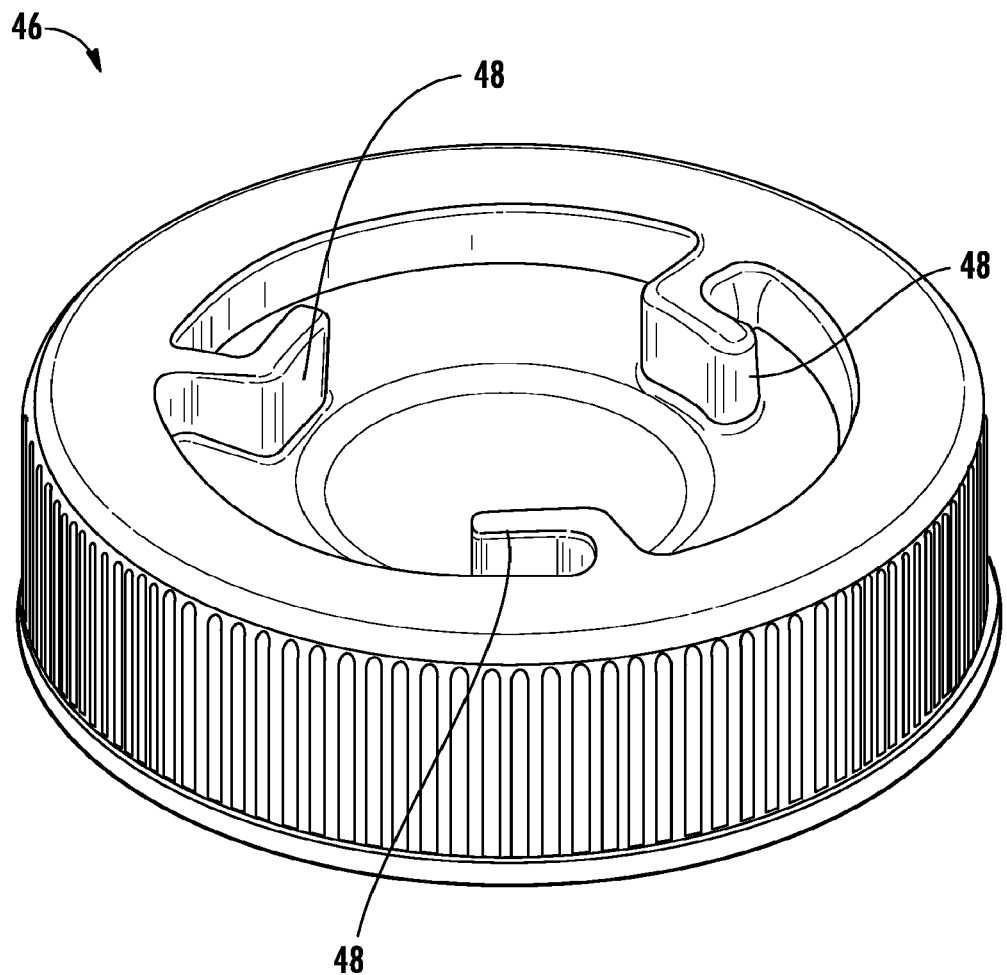
FIG. 6 illustrates a cap of a specimen container configured to store a biological specimen according to some embodiments of the present invention.

According to some embodiments, the tri-star head 134 may engage the cap fingers 48 and rotate the specimen cap 46, while the specimen vial 32 remains stationary. In some embodiments, the specimen vial 32 may include an anti-rotation feature to prevent the rotation of the specimen vial, such as a notch 44, as shown in FIG. 4. For example, the notch 44 may be configured to mate with a reciprocal feature in the sample tray 20 to prevent the specimen vial 32 from rotating when the tri-star head 134 engages the cap fingers 48 of the specimen cap 46. According to some embodiments, the container capper/decapper mechanism 132 may be configured to rotate in a counter-clockwise direction and engage the cap fingers 48 of the specimen cap 46, and may be further configured to remain engaged with the specimen cap. As such, the tri-star head 134 may unscrew and remove the specimen cap 46 from the specimen vial 32 by engaging the specimen cap and moving the tri-star head and the engaged specimen cap in a vertical direction away from the specimen cap. Further, in some embodiments, the anti-rotation feature may be positioned opposite of a longitudinal pocket, such as the first chamber 36, such that the first chamber is disposed at a known particular location when the specimen container 30 is disposed properly within the sample tray.

According to some embodiments, the processing station 120 may further include a molecular capper/decapper mechanism 140, as show in FIG. 10. The molecular tubes 60 may include molecular tube caps 62 with an engagement feature, such as ribs. In some embodiments, the molecular tube caps 62 may further include an anti-rotation feature configured to mate with a reciprocal feature located in the sample tray 20. Accordingly, the molecular tubes 60 may be configured to lock into the sample tray 20 such that when the molecular capper/decapper mechanism 140 engages and rotates a molecular tube cap 62, the molecular tube remains stationary in the sample tray. According to some embodiments, the molecular capper/decapper mechanism 140 may include a chuck having plurality of fingers 142 configured to engage the molecular tube caps 62. In some embodiments, the fingers 142 may be spring loaded fingers, such that when the fingers are lowered onto the molecular tube cap 62, the fingers engage the ribs of the cap and apply a biasing force onto the cap. In addition, the molecular capper/decapper mechanism 140 may be configured to move vertically along the vertical axis of the molecular tube 60. Further, the molecular capper/decapper mechanism 140 may be configured to rotate such that when the chuck is engaged with the molecular tube cap 62, the chuck may rotate counter-clockwise will moving vertically upwards away from the molecular tube 60. According to some embodiments, the molecular capper/decapper mechanism 140 may further include a locking pin 144 configured to engage the top surface of the molecular tube cap 62. In addition, the locking pin 144 may be locked from traveling vertically in the z-axis direction such that when the fingers 142 disengage the molecular tube cap 62 and move upwards away from the molecular tube cap, the fingers are allowed to slip off the molecular tube cap while preventing the molecular tube from being lifted out of the sample tray.

Figure 24:
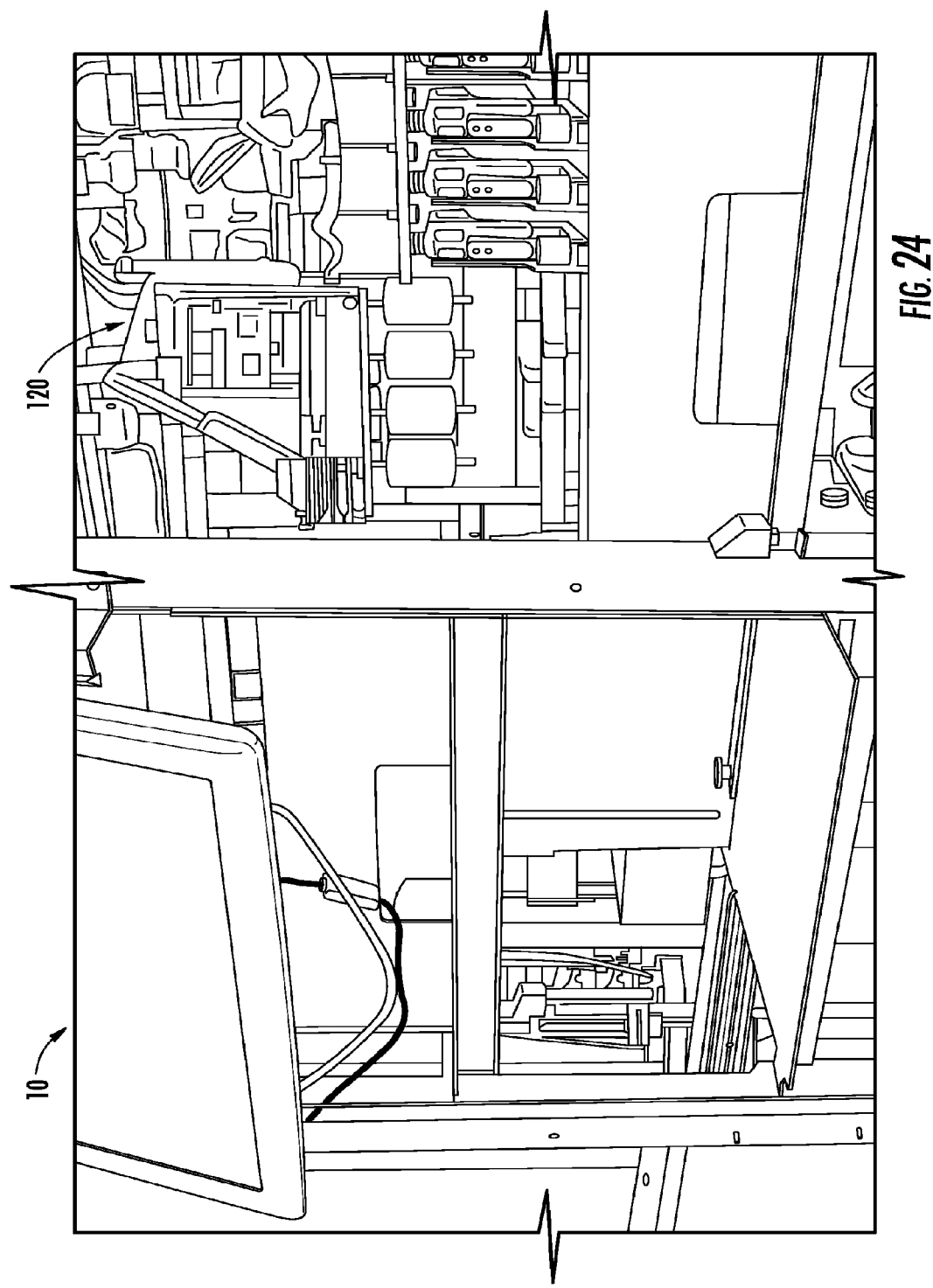
FIG. 24 illustrates a second transport mechanism moving a sample tray according to some embodiments of the present invention.
Figure 25:
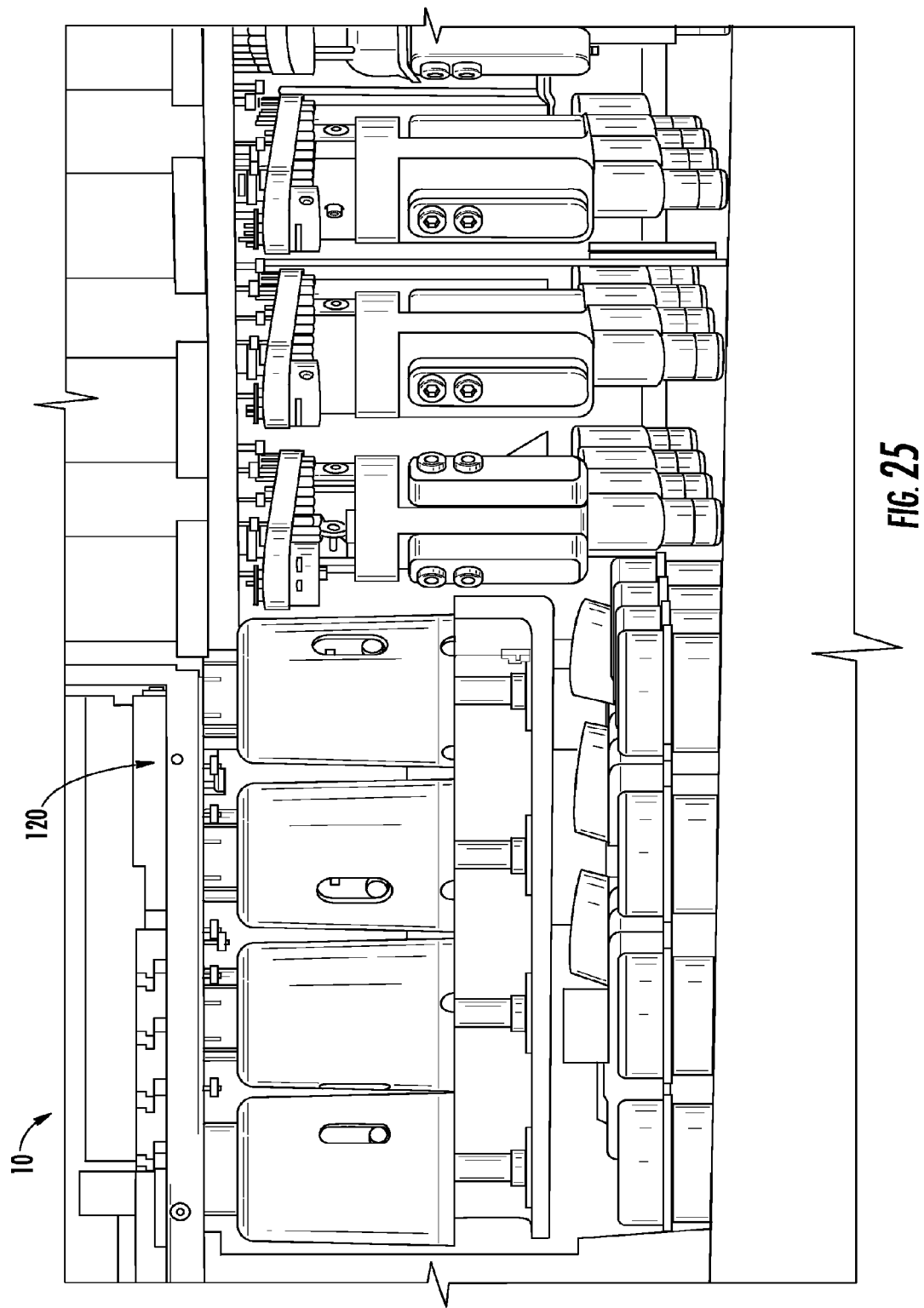
FIG. 25 illustrates a de-capping device engaging a plurality of specimen containers according to some embodiments of the present invention.

According to some embodiments, the molecular capper/decapper mechanism 140 and the plurality of container capper/decapper mechanisms 132 may be configured to move in conjunction with one another (see FIGS. 24-25). In some embodiments, the molecular capper/decapper mechanism 140 and the plurality of container capper/decapper mechanisms 132 may be configured to move downwards towards the respective molecular tubes 60 and specimen containers 30, respectively. As such, the container capper/decapper mechanisms 132 may engage a number of specimen containers 30, wherein each specimen container corresponds to a specific molecular tube 60. In other words, a portion of the sample taken from each container 30 may be dispensed in a specific molecular tube 60. In some embodiments, the molecular capper/decapper mechanism 140 may be configured to engage a row of molecular tubes, the row of molecular tubes having a number of molecular tubes equal to the number of specimen containers disposed in a single row within the sample tray. For example, as shown in FIG. 10, the molecular capper/decapper mechanism 140 may be configured to engage four molecular tubes, and the specimen container de-capping device 130 may include four capper/decapper mechanisms 132, each capper/decapper mechanism configured to engage one of the four specimen containers 30.

The processing station 120 may include a syringe driver or pipetting device 150 configured to select and engage at least one syringe 90 stored within a sample tray 20, as shown in FIG. 10. In some embodiments, the syringe driver 150 may be configured to select and engage a number of syringes 90 stored within the sample tray 20 equal to the number of specimen containers 30 and molecular tubes 60 disposed along a single row within the sample tray. For example, in some embodiments, the syringe driver 150 may be configured to select and engage four syringes 90, wherein each syringe corresponds with a respective specimen container 30, centrifuge tube 84, and/or molecular tube 60. In addition, the syringe driver 150 may be configured to select and pick up at least one syringe 90 from the sample tray 20 for mixing and/or transferring a specimen from a specimen container vial 32 to a molecular tube 60 and/or a centrifuge tube 84. According to some embodiments, the syringe driver 150 may be configured to engage a 12 ml disposable syringe having a narrowed section at the tip opening, wherein the narrowed section at the tip opening provides for shearing the sample specimen fluid disposed within the specimen container, as discussed above.

According to some embodiments, the processing station 120 may further include a density reagent dispenser 160, as shown in FIG. 19. In some embodiments, the density reagent dispenser 160 may be in fluid communication with a density reagent reservoir 162. In some embodiments, the density reagent dispenser 160 may include a dispensing tip and a pump, both of which may be in fluid communication with the density reagent reservoir. According to some embodiments, the density reagent dispenser 160 may be configured to dispense a predetermined amount of density reagent into a centrifuge tube 84 prior to a syringe 90 dispensing a specimen into the centrifuge tube. In some embodiments, the density reagent dispenser 160 may be configured to prime the dispensing tips and fluid lines containing the density reagent during extended idle times to prevent the system from clogging. In some embodiments, the processing station 120 may further include a liquid level sensor, such as an ultrasonic transducer, that may be mounted on the processing station and be configured to detect that a proper amount of density reagent was dispensed into each of the centrifuge tubes 84.

Figure 16:
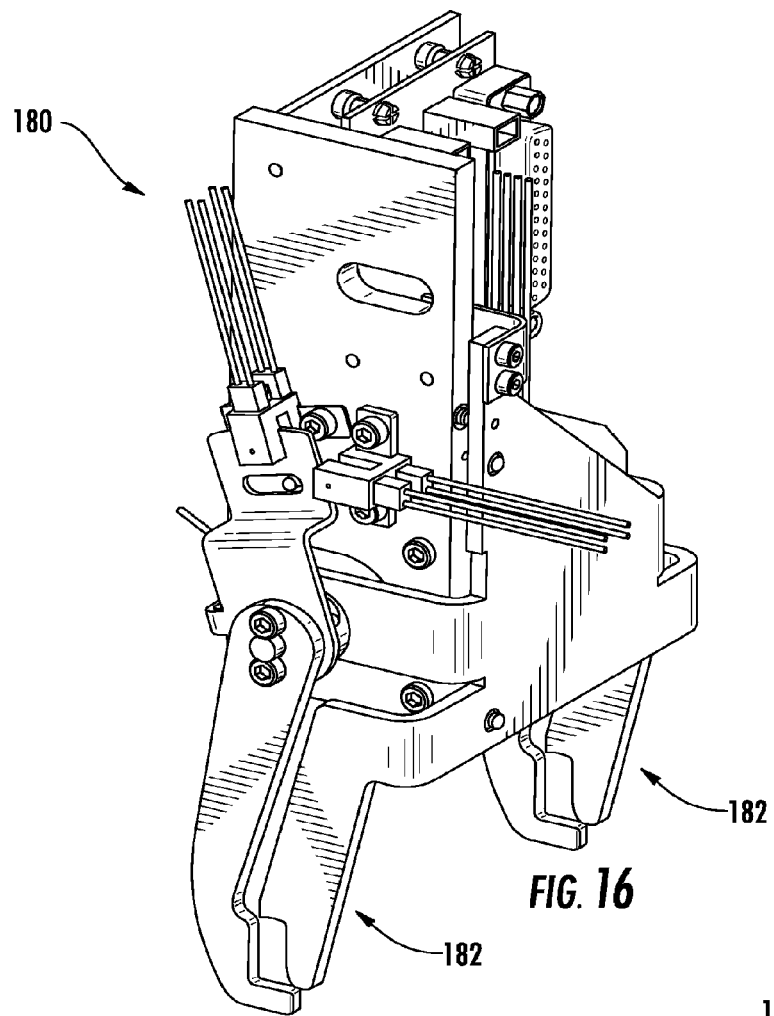
FIG. 16 illustrates a centrifuge tube rack gripper mechanism according to some embodiments of the present invention.
Figures 17A, 17B, 17C, 17D:
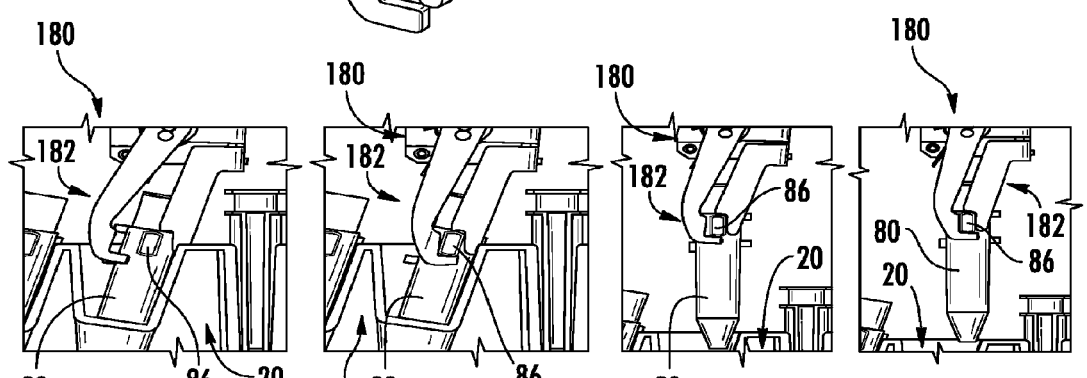
FIG. 17A illustrates a third transport mechanism engaged with a centrifuge tube rack according to some embodiments of the present invention.
FIG. 17B illustrates a third transport mechanism engaged with a centrifuge tube rack according to some embodiments of the present invention.
FIG. 17C illustrates a third transport mechanism engaged with a centrifuge tube rack according to some embodiments of the present invention.
FIG. 17D illustrates a third transport mechanism engaged with a centrifuge tube rack according to some embodiments of the present invention.

According to some embodiments, the processing station 120 may further include a third transport mechanism 180 configured to move one or more centrifuge tubes 84 and/or centrifuge tube racks 80 disposed within the sample tray 20 to and/or from a centrifuge 220, as shown in FIGS. 16-17D. In some embodiments, the third transport mechanism 180 may be configured to move at least one centrifuge tube rack 80 from the sample tray 20 and/or the centrifuge 220 to an aspirate decant station 200 (see FIG. 18). The third transport mechanism 180 may include at least one rack gripper 182 configured to grip the ears 86 of a tube rack 80. In some embodiments, the centrifuge tube rack 80 may be disposed within the sample tray 20 at an angle of between 13 and 15 degrees. Accordingly, the centrifuge rack gripper 182 may be configured to allow for the rotation of the centrifuge tube rack 80 when the gripper is engaged with the centrifuge rack. In some embodiments, the gripper 182 may be configured to rotate the centrifuge rack 80 from an angled position when disposed within a sample tray 20 (see FIGS. 17A-17B) to a substantially vertical position when fully secured by the gripper, as shown in FIGS. 17C-17D. According to some embodiments, the third transport mechanism 180 may further include at least one sensor configured to detect the presence of a centrifuge tube rack 80 when gripped by the gripper 182. In some embodiments, the third transport mechanism 180 may include a leveling device configured to engage a centrifuge bucket of a centrifuge device. In particular, the leveling device of the third transport mechanism 180 may be configured to level the centrifuge bucket when the centrifuge tube racks 80 are being placed within the centrifuge bucket and/or leveling the bucket when taking the centrifuge tube racks out of the bucket that is not leveled after a centrifuge spin cycle.

In addition, the third transport mechanism 180 may be configured to move vertically along the z-axis direction and/or horizontally along the x-axis direction. Specifically, the third transport mechanism 180 may be configured to move vertically along the z-axis direction to select, engage, and/or grip a centrifuge tube rack 80 disposed within the sample tray 20 and remove the centrifuge tube rack from the sample tray. In some embodiments, the third transport mechanism 180 may be configured to move horizontally along the x-axis direction to move the selected centrifuge tube rack 80 from the sample tray 20 to a centrifuge 220. In addition, the third transport mechanism 180 may be configured to move vertically along the z-axis direction so as to deposit a centrifuge tube rack 80 within the centrifuge 220. The third transport mechanism 180 could be any suitable mechanism for moving the centrifuge tube racks 80 in any desired direction, such as a robotic device configured to travel at least in the x-axis and z-axis directions.

According to some embodiments, the system 10 may further include a centrifuge 220, as shown in FIG. 19. In some embodiments, the centrifuge 220 may further include a plurality of centrifuge buckets, wherein each centrifuge bucket is configured to receive a plurality of centrifuge tube racks therein. According to some embodiments, the centrifuge buckets may be configured to receive at least three centrifuge tube racks 80, wherein each centrifuge tube rack is configured to hold four centrifuge tubes 84. In some embodiments, the centrifuge 220 may include four centrifuge buckets allowing for a total of 48 centrifuge tubes to be spun during a single centrifuge spin cycle. In some embodiments, the centrifuge 220 may be configured to spin a specimen sample at approximately 200-800 times the force of gravity.

Figure 18:
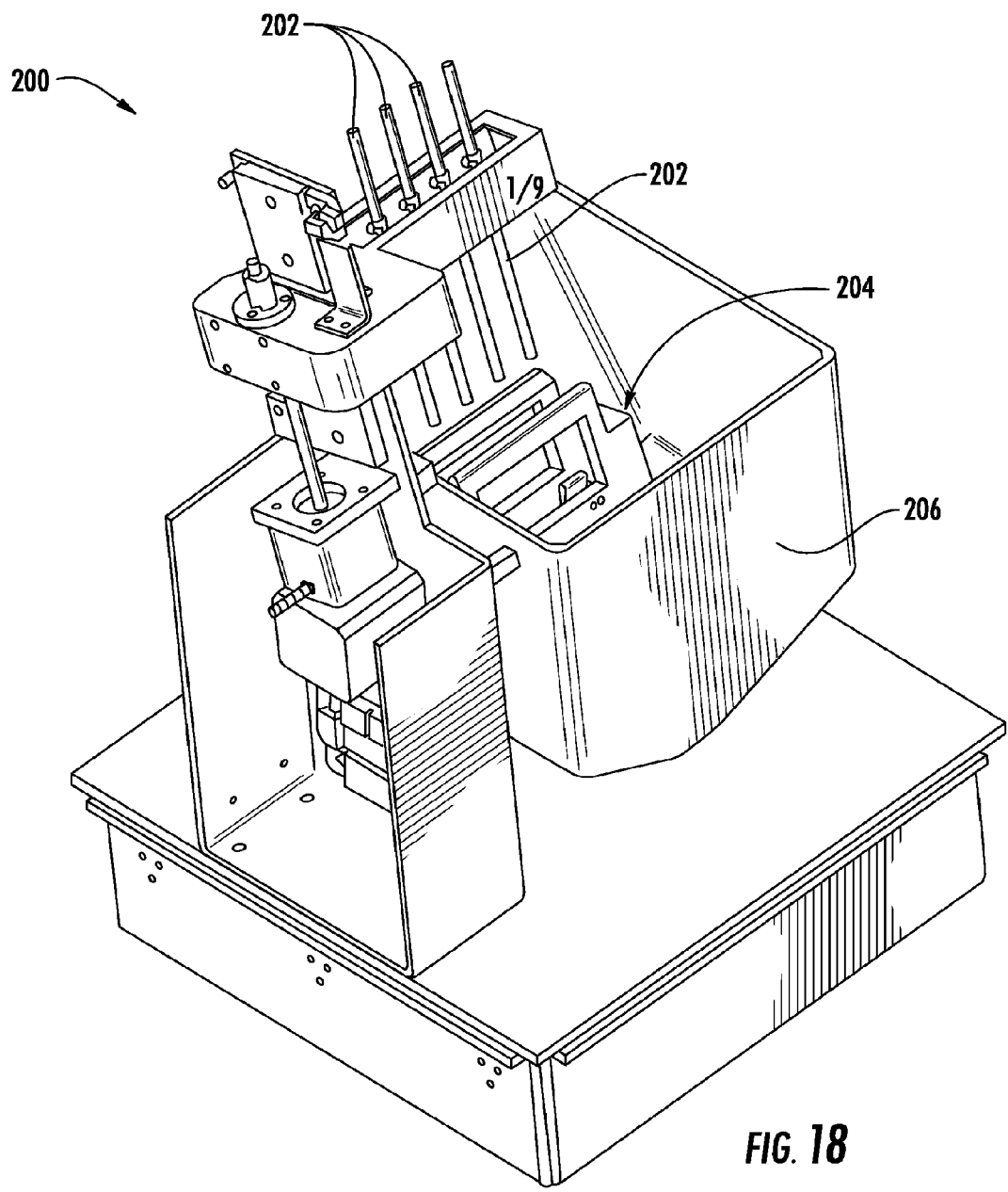
FIG. 18 illustrates an aspirate/decanting station according to some embodiments of the present invention.

According to some embodiments of the present invention, the system 10 may further include an aspirate decant station 200, as shown in FIG. 18. The aspirate decant station 200 may be configured to receive at least one centrifuge tube rack 80 therein. Specifically, the aspirate decant station 200 may include a centrifuge tube rack holder 204 configured to receive the centrifuge tube rack 80 within the aspirate decant station. In some embodiments, the aspirate decant station 200 may also include a plurality of aspiration tips 202. As shown in FIG. 18, the aspirate decant station 200 according to one embodiment may include four aspiration tips 202. The aspiration tips 202 may be configured to move along the vertical axis of a respective centrifuge tube 84. In some embodiments, the aspiration tips 202 may be in fluid communication with a liquid waste container. Further, the liquid waste container may be in fluid communication with a vacuum pump. Accordingly, the aspiration tips 202 may be configured to aspirate waste fluid from the centrifuge tubes 84 after the centrifuge tubes have been subjected to at least one spin cycle. According to some embodiments, the aspirate decant station 200 may be configured to lower the tips 202 during the aspiration cycle at a speed to allow the end of the tips to be disposed slightly below the surface of the liquid waste being aspirated. As such, as the liquid waste is aspirated from the centrifuge tubes 84, the aspiration tips 202 are vertically lowered further along the vertical axis of each of the centrifuge tubes 84.

In some embodiments, the aspiration tips 202 are lowered to a level within the centrifuge tubes to allow for the removal of the waste fluid. In particular, the aspiration tips 202 may be lowered until the tips remove the waste fluid and reach an interface layer between the density reagent and the specimen sample fluid. According to some embodiments, the aspiration tips 202 may include a liquid level sensor configured to detect whether a fluid was removed from the centrifuge tubes 84. In particular, the aspiration tips 202 may include a liquid level sense circuit configured to determine whether the aspiration tips may have been clogged with a solid and/or other contaminant during the aspiration process. In some embodiments, if the tips 202 are clogged during the aspiration process, the aspirate decant station 200 may be configured to pump a wash fluid through the tips in a reverse direction to clear the clog.

According to some embodiments, the tips 202 may be configured to be washed after the aspiration of a waste fluid is completed. For example, the centrifuge tube rack holder 204 may be rotated to a wash position such that the aspiration tips 202 are disposed directly over a wash basin 206. A washing solution may be pumped into the wash basin 206, and the aspiration tips 202 may be lowered into the wash basin. As the aspiration tips 202 are lowered into the wash basin 206, the aspiration tips may aspirate the washing solution through the tips to clear any contaminants and/or rinse any waste fluid within the aspiration tips. According to some embodiments, the liquid level sensor of the aspiration tips 202 may be configured to detect the presence of a washing fluid when the tips are submerged within the washing fluid. Accordingly, the liquid level sensor of the aspiration tips 202 may be configured to alert the user if the aspiration tips are not submerged within the washing fluid.

According to some embodiments, the centrifuge tube rack holder 204 of the aspirate decant station 200 may be configured to move from an aspirating position to a decanting position. Specifically, the centrifuge tube rack holder 204 may be configured to rotate approximately 180 degrees from an aspirating position to a decanting position. In some embodiments, the decanting position may be the same position as the washing position. Accordingly, when a centrifuge tube rack 80 is placed within the centrifuge tube rack holder 204, and the rack holder is moved from the aspirating position to the decanting position, the density reagent remaining within the centrifuge tubes 84 will drain into the wash basin 206. In some embodiments, the aspirate decant station 200 may include a liquid level sensor to determine if the amount of fluid within the wash basin 206 exceeds a pre-determined height. Accordingly, if the liquid level sensor determines that the amount of fluid exceeds the pre-determined height, the sensor may be configured to alert the user that the wash basin 206 has filled to a certain level that may indicate that a wash basin drain is clogged.

According to some embodiments of the present invention, the system 10 may further include a graphical user interface 230, as shown in FIG. 19. In some embodiments, the graphical user interface 230 may include a touch screen configured to receive a user touch input. According to some embodiments, a user may provide the graphical user interface 230 with touch inputs corresponding to the configuration of sample trays 20. In some embodiments, the graphical user interface 230 may be configured to display a system status. In another embodiment, the graphical user interface 230 may be configured to control the internal motions, specimen processing, and/or fluid handling of the system 10.

FIGS. 20A-20B illustrates on embodiment of a system 10 according to embodiments discussed above. In some embodiments, the system 10 may further include additional optional processing modules, as shown in FIGS. 20C-20F. For example, the system 10 may include an optional slide preparation add-on module 240 configured to prepare slides of the specimen sample previously processed with the system 10, as shown in FIGS. 20E-20F. In some embodiments, the system 10 may include an optional molecular tube re-racking module 250 configured to select, engage, and/or store molecular tubes 60 containing a specimen sample stored therein, as shown in FIGS. 20C-20F.

Some embodiments of the present invention provide for a method for automated specimen sample preparation. In particular, FIGS. 21-34 illustrate portions of a method performed by a system 10 configured to provide for the automated specimen sample preparation according to some embodiments. As shown in FIG. 21, a user may first place a sample tray 20 upon an input shelf 103 of a system 10 for further processing. Prior to placing the sample tray 20 within the system 10 for automated processing, a user may prepare the sample tray 20 for the automated processing. In particular, the user may first record identification indicia of the sample tray 20, and identification indicia of each of the molecular tubes 60, centrifuge tubes 84, and/or specimen containers 30. Accordingly, the user may insert an identified centrifuge tube 84 into a respective centrifuge tube rack 80 at a position corresponding to the related identified specimen container. In some embodiments, the user may place the corresponding identified molecular tube 60 into the sample tray 20 at a position corresponding to the related identified specimen container and/or centrifuge tube.

Once the user has placed a sample tray 20 within the input shelf 103, the tray elevator spatula 104 may engage the sample tray and move the sample tray along the horizontal x-axis direction and/or the vertical z-axis direction via a first transport mechanism 105. In some embodiments, as the sample tray 20 is moved along the horizontal x-axis direction (e.g., with the spatula 104), a first imaging device 106, such as a camera, may verify that the each of the specimen containers, molecular tubes, centrifuge tubes, centrifuge tube racks and/or syringes are seated properly within the sample tray, as shown in FIG. 22. For example, the first imaging device 106 may determine the heights of each component in the tray 20 to verify the components are properly seated. In addition, the first imaging device 106 may verify the identity of the sample tray 20 and/or the centrifuge tube racks 80 disposed within the sample tray. According to some embodiments, the second imaging device 108, such as a camera, may verify the identity of the disposables, such as the specimen containers, molecular tubes, and/or centrifuge tubes, within the sample tray. In addition, the system 10 may verify that the disposables are properly positioned within the sample tray and that the disposables are properly assigned to the identified sample tray. In some embodiments, if the disposables are not properly seated, positioned, and/or correlated to the sample tray, the system 10 may be configured to alert the user and/or reject the tray for further processing. As such, the system 10 may suspend operations until the user removes the tray and corrects the problem. In some embodiments, the system 10 may be configured to selectively proceed with the automated processing after recording the error condition, such as the inability to read an identification indicia.

In some embodiments, when the system 10 has verified that the disposables are properly seated, positioned and/or correlated within the sample tray 20, the system 10 may then proceed with the automated processing. As shown in FIG. 23, a first transport mechanism 105 may engage the sample tray 20 (e.g., with the spatula 104 or other engagement device) and may be configured to move at least horizontally in the x-axis direction and vertically in the z-axis direction.

In some embodiments, the first transport mechanism may move the sample tray 20 from the elevator to a processing deck 121. For example, the first transport mechanism may position the sample tray 20 on the processing deck, and a second transport mechanism 122 may then convey the sample tray to a first processing location, as shown in FIGS. 23-24, along the x-axis direction. The first transport mechanism 105 could be any suitable mechanism for moving the sample trays 20 in any desired direction, such as a robotic device configured to travel at least in the x-axis and z-axis directions. The processing deck may include one or more engagement features for engaging the bottom surface of the sample tray 20 during processing. Once the sample tray is located at a first processing location, a third imaging device may verify the identity of the specimen container, as shown in FIG. 24.

According to some embodiments, the second transport mechanism 122 may be further configured to move the sample tray 20 at least horizontally along the y-axis direction (in addition to the x-axis direction) between the first processing location and the second processing location. The first processing location may correspond to a location on the processing deck where the tray is positioned thereon and the components within the sample tray are configured to be accessed (e.g., for capping/de-capping and pipetting), while the second processing location may correspond to a different location where the tray may be accessed by the third transport mechanism (e.g., for centrifugation). The second transport mechanism 122 could be any suitable mechanism for conveying the sample trays 20 in any desired direction, such as a conveyor mechanism for moving the trays in the x-axis and y-axis directions.

Further, in some embodiments, the second transport mechanism 122 may move the sample tray along the y-axis direction to ensure that the tips 164 of the density reagent dispenser 160 are aligned with the centrifuge tubes for dispensing the appropriate amount of density reagent into each of the centrifuge tubes. In some embodiments, the density reagent dispenser may dispense approximately 4 ml of the density reagent. A liquid level sensor 168 may then check to ensure that the proper amount of density reagent has been dispensed into each of the centrifuge tubes. If an incorrect level of density reagent is found within any of the centrifuge tubes, the system may notify the user, and/or halt operations until the user has corrected the problem.

Figure 26:
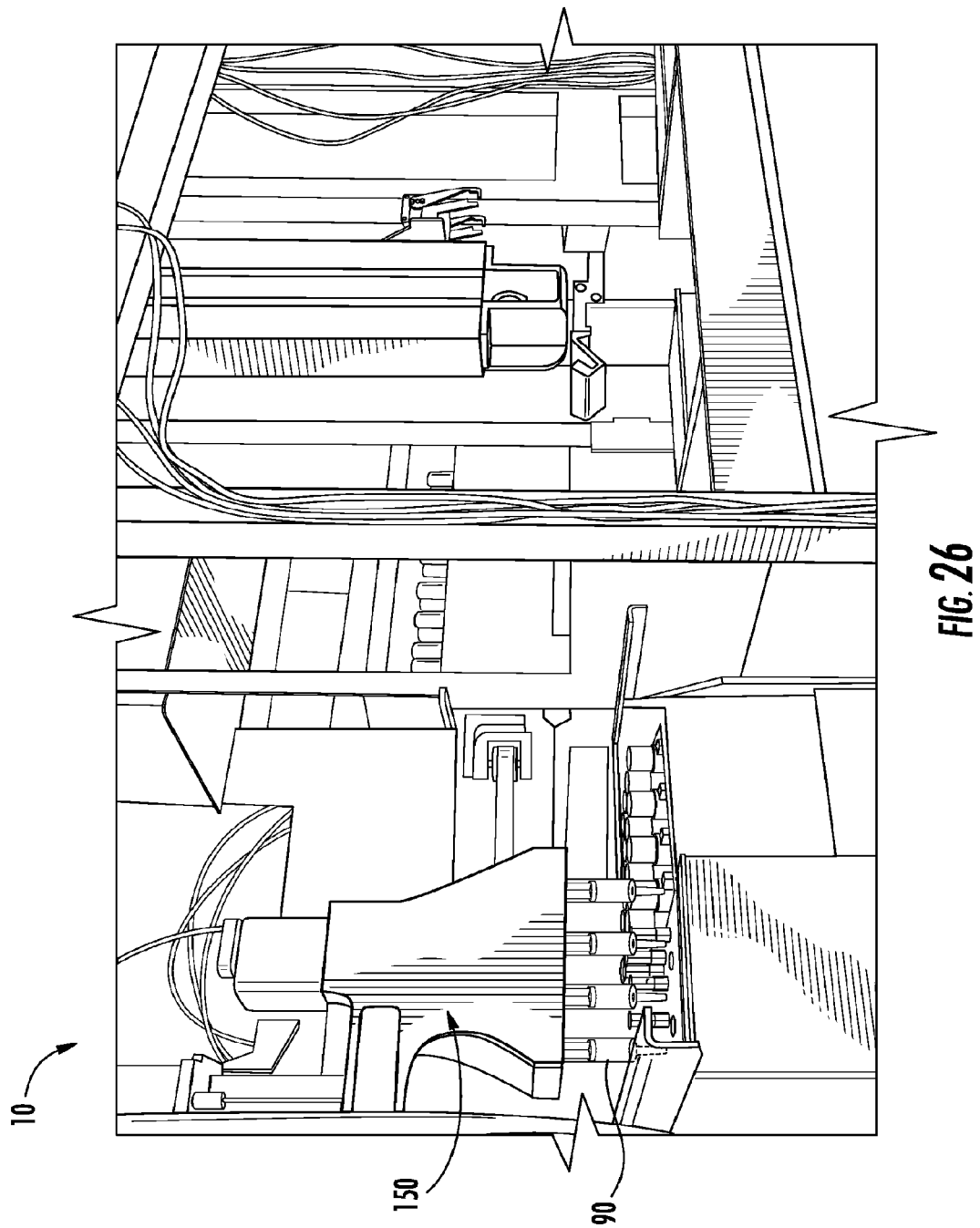
FIG. 26 illustrates a pipetting device selecting and engaging a plurality of syringes according to some embodiments of the present invention.
Figure 27:
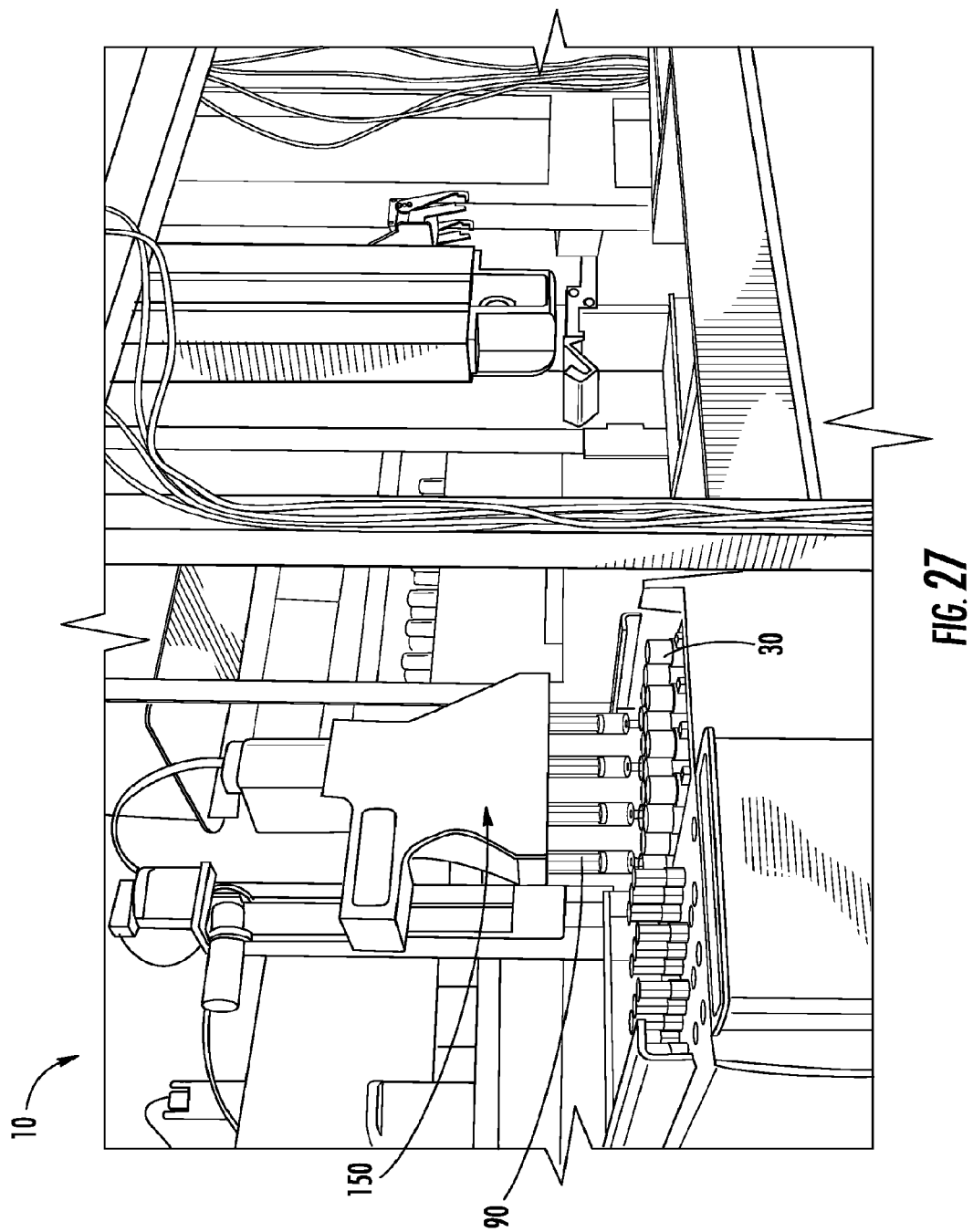
FIG. 27 illustrates a pipetting device engaging a plurality of syringes according to some embodiments of the present invention.

In some embodiments, the specimen container de-capping assembly 130 and the molecular tube de-capping assembly 140 may then de-cap the specimen containers, as shown in FIG. 25. As shown in FIG. 26, the syringe driver or pipetting device 150 may then select and engage a respective syringe 90 corresponding to each of the de-capped specimen containers. The system may then cause the syringes to be inserted within the specimen container and mix the specimen sample therein, as shown in FIG. 27. The syringes may then aspirate approximately 8.5 ml of the specimen sample from each of the respective specimen containers and deposit approximately 0.5 ml of the specimen sample within the molecular tube. According to some embodiments, the liquid level sensor 168 may be configured to measure the liquid levels of the molecular tubes. In some embodiments, the liquid level sensor may be configured to alert the user and/or halt the automated processing if an incorrect amount of liquid has been deposited into any one of the molecular tubes.

Figure 28:
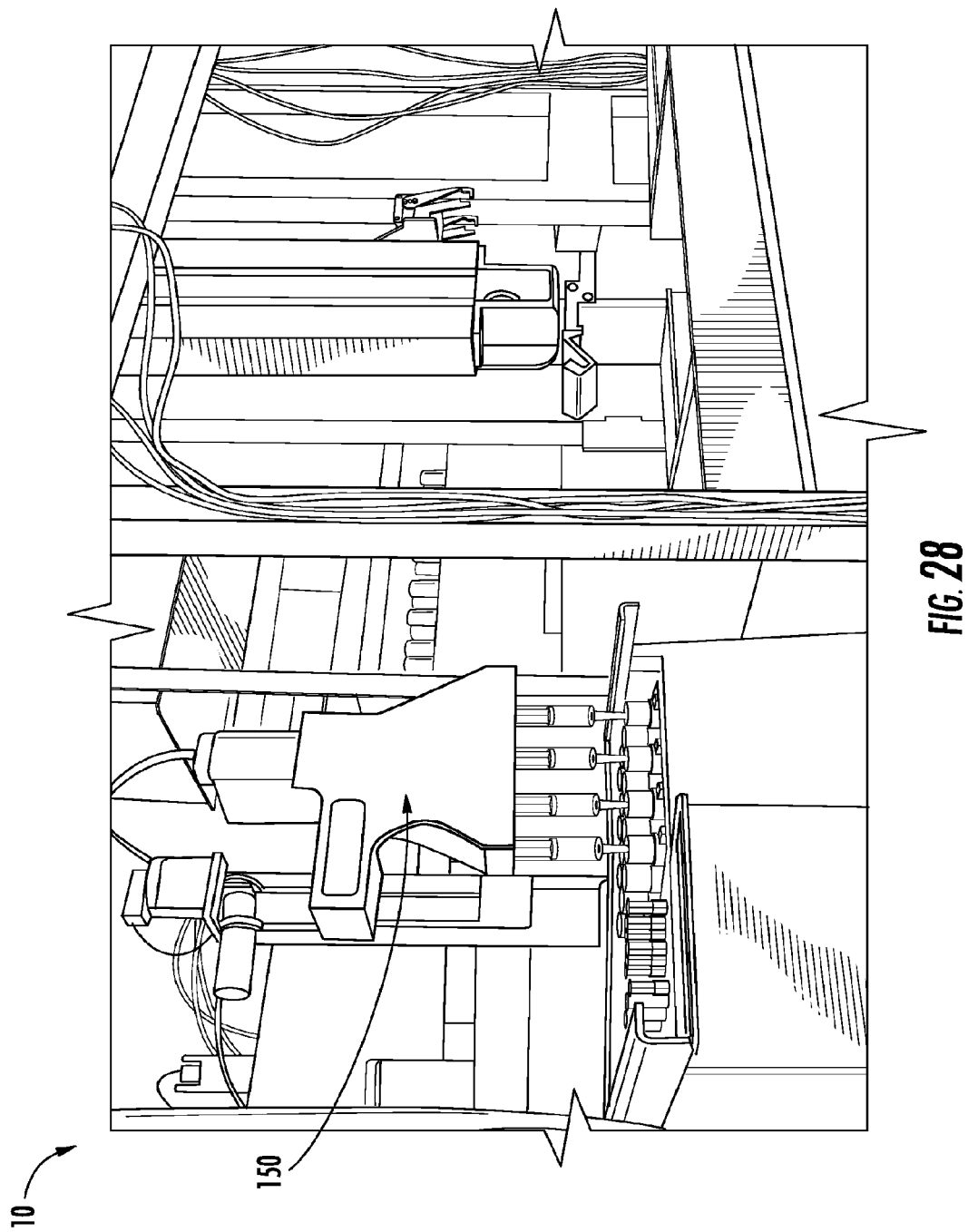
FIG. 28 illustrates a pipetting device engaging a plurality of syringes according to some embodiments of the present invention.
Figure 29:
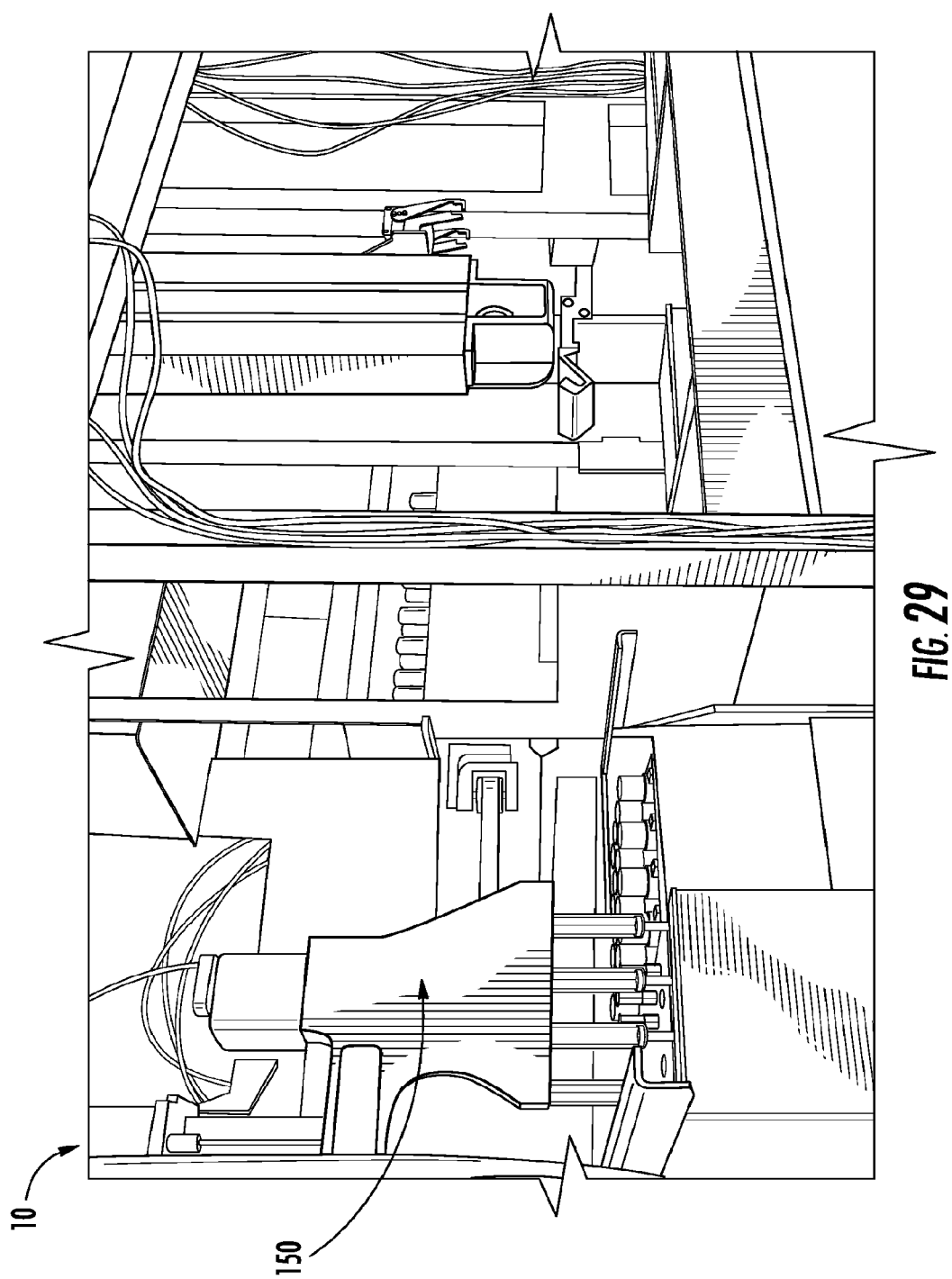
FIG. 29 illustrates a pipetting device discarding a plurality of syringes according to some embodiments of the present inventions.

As shown in FIG. 28, the syringes may then dispense approximately 8 ml of the specimen into each of the corresponding centrifuge tubes. Again, the liquid level sensor 168 may be configured to measure the liquid levels of the centrifuge tubes. In some embodiments, the liquid level sensor may be configured to alert the user and/or halt the automated processing if an incorrect amount of liquid has been deposited into any one of the centrifuge tubes. After dispensing the specimen into the centrifuge tubes, the syringe driver may eject the syringes into a waste bin to ensure a single syringe is used for a single sample and to prevent cross contamination, as shown in FIG. 29.

Figure 30:
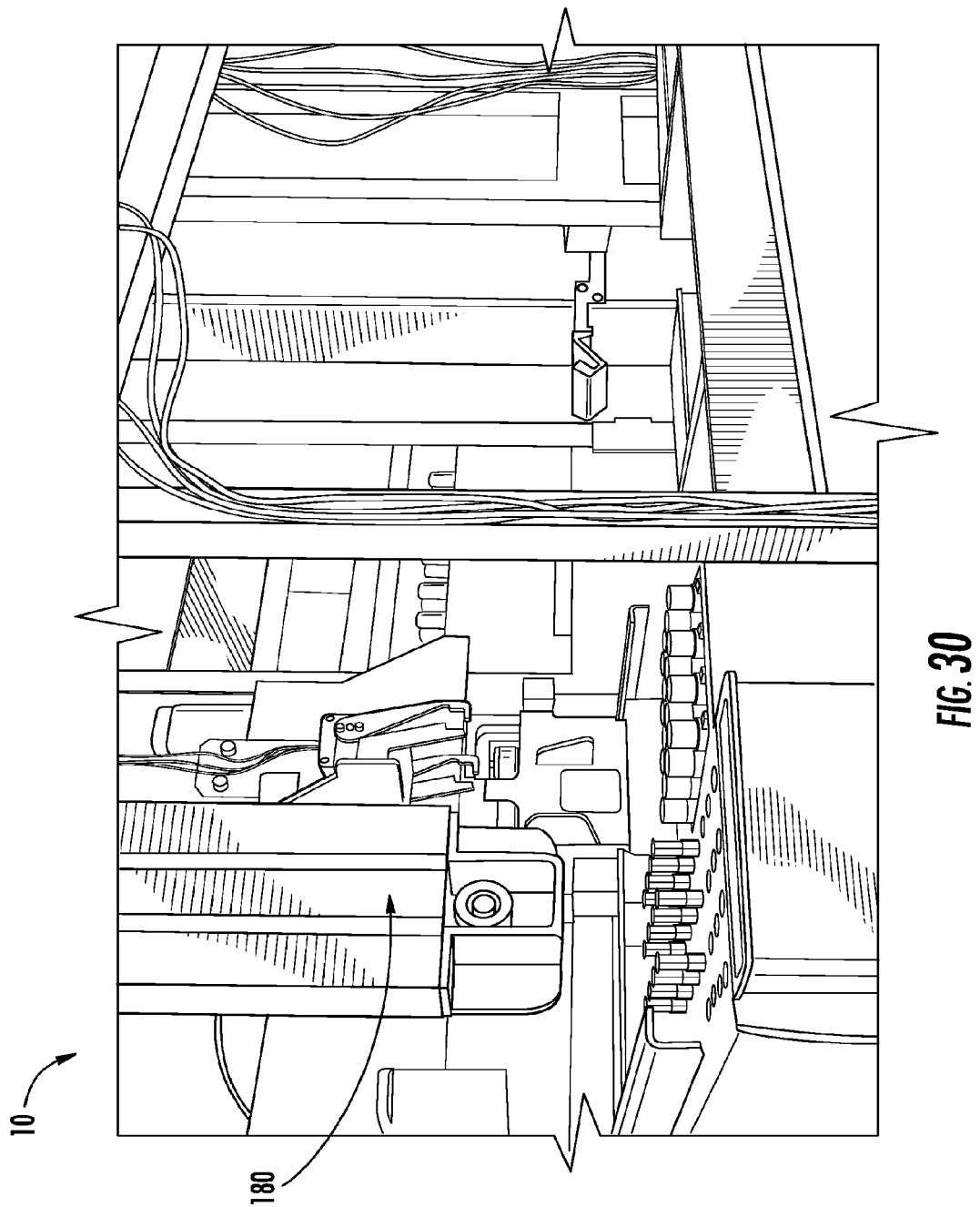
FIG. 30 illustrates a third transport mechanism selecting a centrifuge tube rack according to some embodiments of the present invention.
Figure 31:
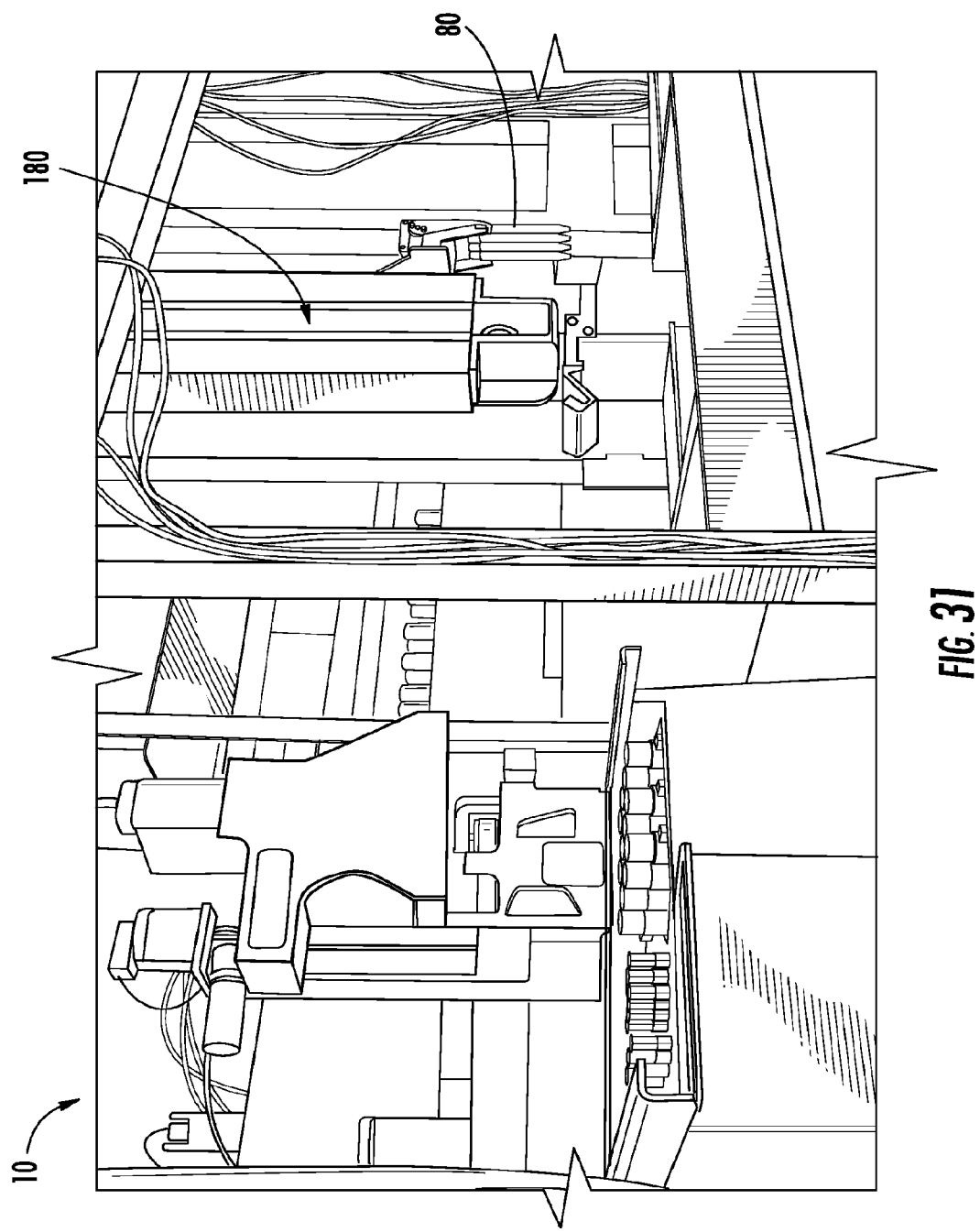
FIG. 31 illustrates a third transport mechanism transporting a centrifuge tube rack according to some embodiments of the present invention.
Figure 32:
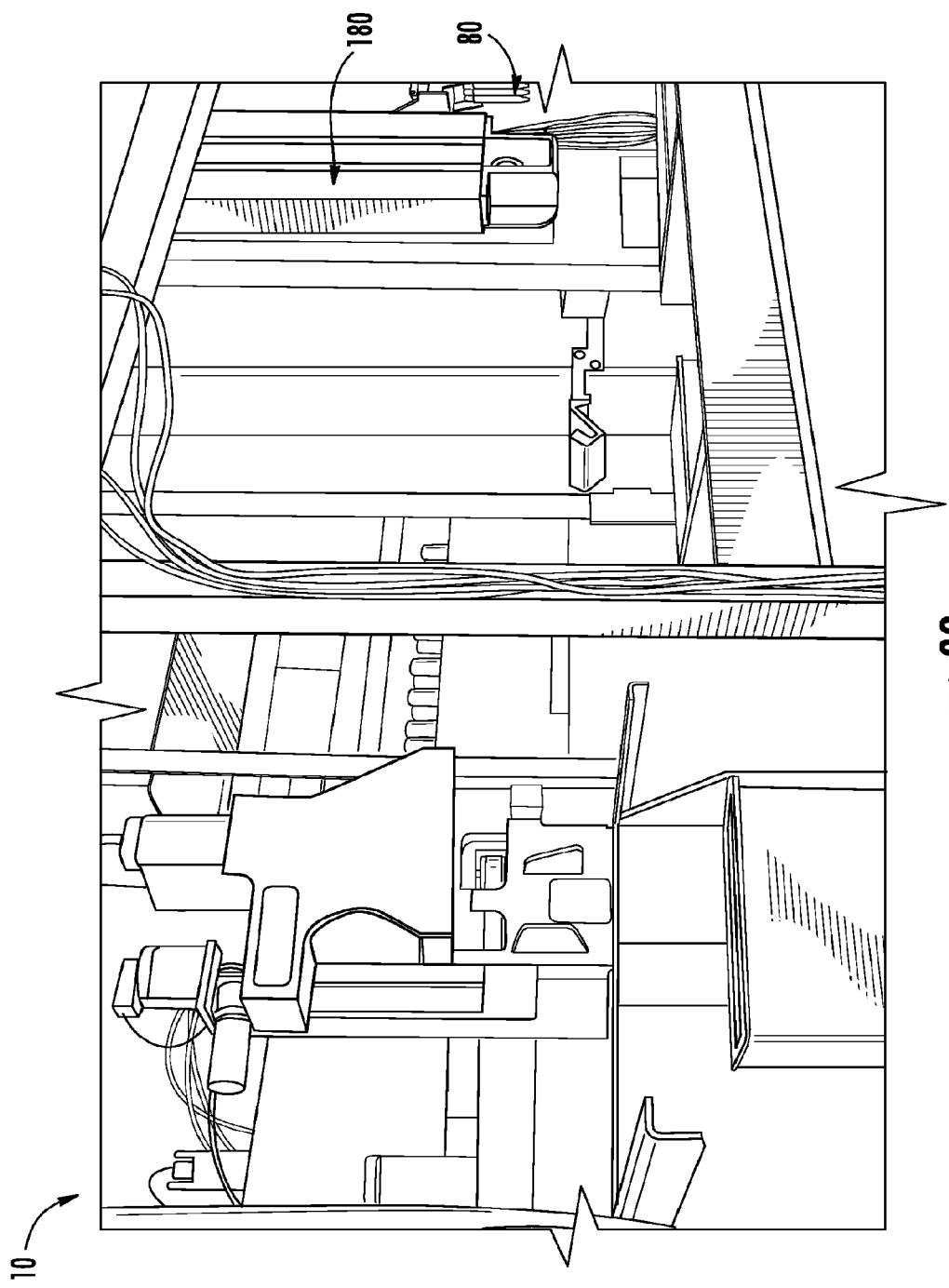
FIG. 32 illustrates a third transport mechanism transporting a centrifuge tube rack according to some embodiments of the present invention.

According to some embodiments, a third transport mechanism 180 may then select and engage a centrifuge tube rack to be transported to a centrifuge, as shown in FIGS. 30 and 31. After all of the racks have been transported to the centrifuge, the centrifuge may then spin imparting a force approximately 200 times the force of gravity. The third transport mechanism may then select and engage the centrifuge tube rack to be transported to an aspirate decant station, as shown in FIG. 32.

Figure 33:
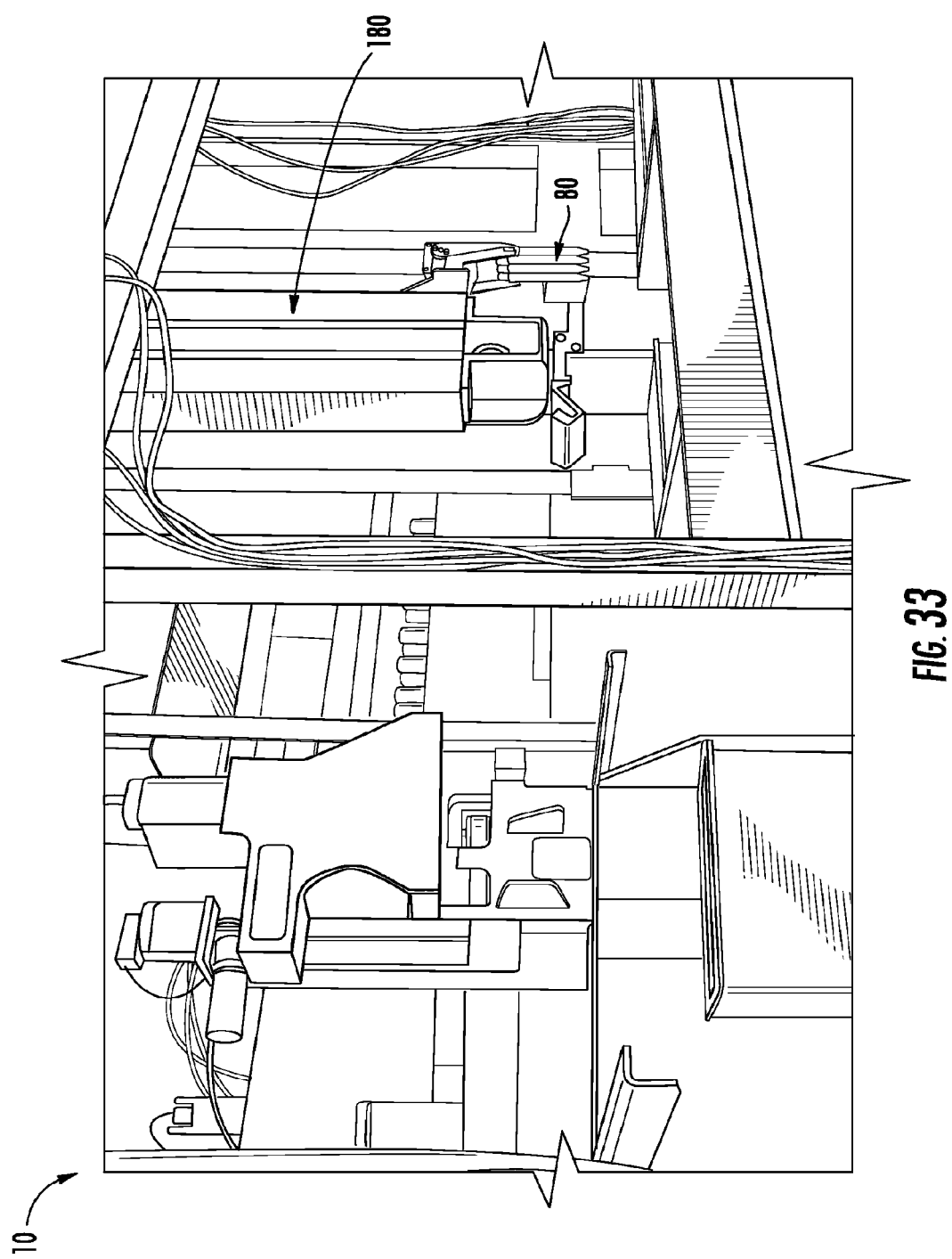
FIG. 33 illustrates a third transport mechanism transporting a centrifuge tube rack according to some embodiments of the present invention.

According to some embodiments, a waste bottle vacuum pump fluidly connected to the tips may engage, and the tips may be moved down into the centrifuge tubes so as to aspirate the waste fluid from the tubes. When the tips are withdrawn from the centrifuge tubes, the liquid level will be checked. In some embodiments, the centrifuge rack may be placed back into the centrifuge by the third transport mechanism, as shown in FIG. 33, if the tips did not clog for a secondary spin. In some embodiments, the centrifuge may be configured to impart a force approximately 800 times the force of gravity during a secondary spin.

If waste liquid is found in one or more centrifuge tubes, the rack may be picked up and stored into the buffer, as shown in FIG. 19. The aspirate decant station will back flush the aspiration tips to unclog the tips, and then the third transport mechanism will re-load the centrifuge rack to reattempt the aspiration process. In some embodiments, the system may alert the user and/or halt the automated processing operations if the liquid level sensor detects that waste fluid still exists within the centrifuge tube.

Once a secondary spin has been completed, the third transport mechanism may be configured to select and engage a centrifuge tube rack so as to decant the density reagent. In one embodiment, as shown in FIG. 34, the centrifuge tube rack transportation mechanism may select and engage a centrifuge tube rack and transport the rack back to the aspirate decant station. The aspirate decant station may be configured to decant the density reagent from each of the centrifuge tubes. In some embodiments, the system may be configured to alert the user and/or halt operations if a liquid level sensor of a wash basin of the aspirate decant station indicates that the liquid level has reached a pre-determined threshold, which may indicate that a drain valve of the wash basin is clogged, inoperative and/or otherwise disabled.

According to some embodiments, after the centrifuge tubes have been properly decanted, the centrifuge tube racks containing the prepared specimen sample are returned to the sample trays for further processing. The trays may then be transported back to the first processing location and into the elevator. In some embodiments, the system may include additional optional modules configured to further process the specimen sample. For example, a slide preparation module may be configured to prepare slides of the specimen sample from the specimens disposed within the centrifuge tubes.

Accordingly, embodiments of the present invention may provide a number of advantages, such as ensuring the proper chain-of-custody of a specimen sample throughout processing steps prior to analysis of the specimen sample. For example, embodiments of the present invention may include a plurality of imaging devices to ensure that a specimen sample taken from a specimen container will be placed, processed, and/or otherwise correlated to the proper corresponding centrifuge tube and/or molecular tube. In addition, embodiments of the present invention may advantageously provide for the minimization of contamination by ensuring a single specimen container is associated with a corresponding centrifuge tube, molecular tube, and/or syringe. Further, some embodiments of the present invention may provide for the washing of an aspiration tip to ensure that cross-contamination of samples is minimized.

In some embodiments, the system may advantageously facilitate the efficient processing of a number of specimen samples by providing for a number of specimen samples to be processed. For example, a single sample tray may include at least 16 specimen samples according to some embodiments. In addition, the system may be configured to store approximately two full batches of specimens for automated processing totaling approximately 96 specimen samples. Accordingly, the system may advantageously provide for efficient automated processing by including and monitoring a large number of specimen samples for processing.

Many modifications and other embodiments of the invention set forth herein will come to mind to one skilled in the art to which these embodiments pertain having the benefit of the teachings presented in the foregoing descriptions and the associated drawings. Therefore, it is to be understood that the above-described embodiments are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for automated sample preparation comprising:
   providing a plurality of trays, the trays carrying:
      at least one sample container containing a sample and having a respective cap engaged therewith; and
      at least one centrifuge tube rack carrying a plurality of centrifuge tubes;
   automatically transporting the trays to a processing deck;
   automatically reading an identifier on the at least one sample container wherein reading the identifier on the sample container further comprises reading the identifier at a first processing location with a chain-of-custody device;
   automatically removing the cap from the respective sample container;
   automatically removing a portion of the sample from the at least one de-capped sample container;
   automatically dispensing the removed portion of the sample into one of the plurality of centrifuge tubes;
   automatically transporting the at least one centrifuge tube rack to a centrifuge device;
   automatically centrifuging the centrifuge tube containing the sample with the centrifuge device;
   conveying the trays between a first processing location and a second processing location along a Y-direction with a first transport mechanism,
   wherein one of the trays is located at the first processing location when automatically removing the cap from the respective sample container, and
   wherein one of the trays is located at the second processing location when it is accessible by a second transport mechanism, the second transport mechanism transporting the at least one centrifuge tube rack to the centrifuge device;
   transporting the at least one centrifuge tube rack from the centrifuge device to one of the trays located on the processing deck with a third transport mechanism;
   transporting one of the trays from the processing deck to a location external to an elevator reachable by a first transport mechanism with a second transport mechanism; and
   transporting one of the trays from the location external to the elevator reachable by the first transport mechanism into the elevator with the first transport mechanism.

2. The method of claim 1, wherein the trays also carry at least one molecular tube having a respective cap engaged therewith.

3. The method of claim 2, further comprising removing the cap from the at least one molecular tube with a de-capping device.

4. The method of claim 3, further comprising removing a portion of the sample from the at least one de-capped sample container with a pipetting device and dispensing the removed portion into the at least one de-capped molecular tube.

5. The method of claim 1, further comprising removing the cap from the at least one sample container while the at least one sample container is disposed within one of the trays.

6. The method of claim 1, further comprising transporting at least one of the plurality of centrifuge tubes from the centrifuge device to an aspirating and decanting device following the centrifuge operation for aspirating or decanting the at least one of the plurality of centrifuge tubes.

7. The method of claim 1, wherein the step of automatically transporting the trays to the processing deck further comprises engaging a bottom surface of the trays, one at a time, with a transport mechanism, and moving the trays in both an X-direction and a Z-direction.

8. The method of claim 1, further comprising transporting at least one of the plurality of centrifuge tubes from the tray at the second processing location to the centrifuge device in both an X-direction and a Z-direction.

9. The method of claim 1, further comprising disposing each of the at least one centrifuge tube rack within at least one of the trays at an angle of between about 13 and about 15 degrees relative to an axis transverse to a bottom surface of the tray.

10. The method of claim 1, further comprising transporting the trays between a first processing location and a second processing location to facilitate access to each of the at least one centrifuge tube rack and plurality of centrifuge tubes with a transport mechanism.

11. The method of claim 1, further comprising reading an identifier on the trays and the at least one centrifuge tube rack in an elevator with a chain-of custody device prior to transporting the trays to the processing deck.

12. The method of claim 11, further comprising determining whether each of the plurality of centrifuge tubes and the at least one centrifuge tube rack are properly positioned within the trays with the chain-of custody device.

13. The method of claim 12, further comprising reading an identifier on each of the plurality of centrifuge tubes with a second chain-of custody device.

14. The method of claim 1, further comprising:
engaging a disposable syringe disposed in one of the trays; and
after automatically removing the cap from the sample container, removing a portion of the sample from the de-capped sample container with the disposable syringe.

15. The method of claim 14, further comprising disengaging the disposable syringe following use.

16. The method of claim 1, further comprising mixing the sample in the de-capped container prior to removing the portion of the sample from the decapped sample container.

17. The method of claim 1, further comprising simultaneously removing a plurality of caps from a plurality of respective sample containers at a first processing location with a de-capping device.

18. The method of claim 17, further comprising simultaneously removing a portion of the sample from each of the de-capped plurality of containers and simultaneously dispensing the removed portion of the sample into a plurality of centrifuge tubes disposed in a plurality of centrifuge tube racks with a pipetting device.

19. The method of claim 1, further comprising supporting at least one of the plurality of trays on each shelf of a plurality of shelves in an elevator prior to transporting the plurality of trays to the processing deck.

\* \* \* \* \*